(12) United States Patent
Hayakawa et al.

(10) Patent No.: US 9,952,235 B2
(45) Date of Patent: Apr. 24, 2018

(54) STANDARD SOLUTION FOR USE IN ANALYSIS OF AMINO ACIDS IN PLASMA

(71) Applicants: WAKO PURE CHEMICAL INDUSTRIES, LTD., Osaka (JP); AJINOMOTO CO., INC., Tokyo (JP)

(72) Inventors: Masako Hayakawa, Tokyo (JP); Kazutaka Shimbo, Kanagawa (JP); Hiroo Yoshida, Kanagawa (JP)

(73) Assignees: WAKO PURE CHEMICAL INDUSTRIES, LTD., Osaka (JP); AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/450,135

(22) Filed: Mar. 6, 2017

(65) Prior Publication Data

US 2017/0261524 A1    Sep. 14, 2017

Related U.S. Application Data

(62) Division of application No. 14/232,073, filed as application No. PCT/JP2012/068302 on Jul. 19, 2012, now Pat. No. 9,638,706.

(30) Foreign Application Priority Data

Jul. 21, 2011    (JP) ................. 2011-160364

(51) Int. Cl.
   *G01N 33/96* (2006.01)
   *G01N 33/68* (2006.01)
   *G01N 30/04* (2006.01)

(52) U.S. Cl.
   CPC ......... *G01N 33/96* (2013.01); *G01N 33/6806* (2013.01); *G01N 33/6848* (2013.01); *G01N 2030/042* (2013.01); *G01N 2496/80* (2013.01); *Y10T 436/105831* (2015.01); *Y10T 436/106664* (2015.01)

(58) Field of Classification Search
   CPC ............ G01N 2030/042; G01N 33/68; G01N 33/6806; G01N 33/6848; G01N 33/48; G01N 33/96; G01N 2496/00; G01N 2496/80
   USPC ...... 436/8, 15, 16, 63, 86, 89, 90, 161, 173; 252/408.1
   See application file for complete search history.

(56) References Cited

U.S. PATENT DOCUMENTS

| | | | |
|---|---|---|---|
| 3,856,471 A | 12/1974 | Winitz et al. | |
| 9,638,706 B2* | 5/2017 | Hayakawa | G01N 33/6806 |
| 2004/0139943 A1 | 7/2004 | Kern et al. | |
| 2006/0183238 A1 | 8/2006 | Nimkar et al. | |
| 2007/0269899 A1* | 11/2007 | Shimbo | G01N 30/88 436/89 |
| 2010/0140467 A1 | 6/2010 | Goldman | |
| 2011/0143445 A1* | 6/2011 | Daniels | C07D 403/12 436/90 |
| 2012/0238030 A1* | 9/2012 | Rappold | B01D 15/305 436/89 |

FOREIGN PATENT DOCUMENTS

| | | |
|---|---|---|
| JP | 2007-198898 A | 8/2007 |
| JP | 2010-532481 A | 10/2010 |
| JP | 2011-105728 A | 6/2011 |
| WO | WO 2003/069328 A1 | 8/2003 |
| WO | WO 2009/006338 | 1/2009 |

OTHER PUBLICATIONS

Piraud et al. Rapid Communications in Mass Spectrometry, vol. 19, 2005, pp. 1587-1602.*
Piraud et al. Rapid Communications in Mass Spectrometry, vol. 19, 2005, pp. 3287-3297.*
International Search Report for PCT Application No. PCT/JP2012/068302; dated Sep. 25, 2012 (English translation).
Written Opinion of the International Search Authority in PCT Application No. PCT/JP2012/068302; dated Sep. 25, 2012 (English translation).
International Preliminary Report on Patentability for PCT Application No. PCT/JP2012/068302; dated Jan. 21, 2014 (English translation).
Bennett, B.D. et al., "Absolute metabolite concentrations and implied enzyme active site occupancy in *Escherichia coli*," *Nat. Chem. Biol.*, 5(8): 593-599 (2009).
McGaw. E.A. et al., "Comparison of orthogonal liquid and gas chromatography-mass spectrometry platforms for the determination of amino acid concentrations in human plasma," *J. Chromatography A*, 1217: 5822-5831 (2010).

(Continued)

*Primary Examiner* — Maureen Wallenhorst
(74) *Attorney, Agent, or Firm* — Finnegan, Henderson, Farabow, Garrett & Dunner LLP (57) ABSTRACT

An external standard solution for use in the analysis of amino acid in plasma, containing,
(1) at least one amino acid selected from the following components A, at a concentration of 0.0007 M to 0.49 M, and (2) (i) at least one amino acid selected from the following components B, at a concentration of 0.2 to 0.9 times of the lowest-concentration amino acid among the amino acids selected from components A, (ii) at least one amino acid selected from the following components C, at a concentration of 0.1 to 0.4 times of the lowest-concentration amino acid among amino acids selected from the components A, or (iii) at least one amino acid selected from the following components D, at a concentration of 0.05 to 0.2 times of the lowest-concentration amino acid among amino acids selected from the components A;
[Components A] valine, glycine, alanine and glutamine
[Components B] serine, proline, threonine, taurine, leucine, isoleucine, lysine, histidine, phenylalanine and tyrosine
[Components C] asparagine, ornithine, arginine and tryptophan
[Components D] glutamic acid, methionine, citrulline and cystine.

15 Claims, 1 Drawing Sheet

(56) References Cited

OTHER PUBLICATIONS

Shimbo, K. et al., "Precolumn derivatization reagents for high-speed analysis of amines and amino acids in biological fluid using liquid chromatography/electrospray ionization tandem mass spectrometry," *Rapid Commun. Mass Spectrom.*, 23: 1483-1492 (2009).
"Amino acid analysis (39 types) [LC/MS]" http://www.srl.info/srlinfo/kensa_ref_CD/KENSA/SRL6354.htm (Copyright 2011).
NIST, Material Measurement Laboratory, "Development of a Standard Reference Material for Metabolites in Plasma," http://www.nist.gov/cstl/analytical/organic/metabolitesinserum.cfm (May 5, 2011).
Chase, D.H., et al., "Validation of Accuracy-based Amino Acid Reference Materials in Dried-Blood Spots by Tandem Mass Spectrometry for Newborn Screening Assays," *Clinical Chemistry*, 45(8):1269-1277 (1999).

\* cited by examiner

STANDARD SOLUTION FOR USE IN ANALYSIS OF AMINO ACIDS IN PLASMA

This application is a divisional of U.S. application Ser. No. 14/232,073, filed Oct. 7, 2014, now U.S. Pat. No. 9,638,706, issued May 2, 2017, which is a U.S. National Stage Application of PCT Application No, PCT/JP2012/068302, filed Jul. 19, 2012, which claims priority from Japanese Application No. 2011-160364, Filed Jul. 21, 2011, all of which are incorporated herein by reference.

TECHNICAL FIELD

The present invention relates to a standard solution for amino acid analysis, in particular, relates to a standard solution for use as an external or an internal standard substance, and a method for quantitative method of amino acid using the same.

BACKGROUND ART

In recent years, it turned out that metabolites in living organisms have been affected not only by genetic factors but by many environmental factors, and analysis of these metabolite has attracted attention as a guideline for diagnosis of diseases and for health condition, as well as for the analysis of genes and proteins. Among them, amino acid related compounds such as amino acids and amines are one of the metabolite groups existing in most large quantity (see, for example, Non-patent literature 1), the quantitative analyses thereof have been carried out for many years, and various methods of analysis have been developed.

On the other hand, in the quantitative analysis, usually, the calibration curve method, in which a calibration curve is made up by analyzing standard substances with multiple concentrations by interleaving a calibration point of the compound to be analyzed, is generally employed. In the quantitative analysis by such a calibration curve method, correlation between concentration and signal (specifically, a signal which indicates a peak area, peak height, etc.) is determined beforehand using external standard with known concentration, and the concentration in a specimen sample is determined based on the information (that is, the calibration curve) obtained thereupon. Therefore, in the quantitative analysis using the calibration curve method, the reference standard for quantitative determination will be quite important to achieve the analysis with high degree of accuracy since the calibration curve obtained from external standard (criteria) serves as a criteria. And, in order to carry out quantitative analysis by the calibration curve method with high degree of accuracy, it will be essential for performing highly accurate quantitative method that a series of several different concentrations of the reference standard is prepared, and a calibration curve is made up actually by using them, and the concentration of measuring object in a specimen sample fits within the concentrations of the reference standard which are used to make up the calibration curve. Specifically, if the concentration of the object in a specimen sample is 50 $\mu$M mol/L), it is preferable to use the standard substance of 25 $\mu$M to 75 $\mu$M. Furthermore, the range of calibration points (calibration points) of reference standard in this case, is preferable to be narrow since the linearity between concentration and signal can easily be secured. In more specifically, it is more desirable to take the calibration points from 25 $\mu$M to 75 $\mu$M rather than to take the calibration points from 1 $\mu$M to 100 $\mu$M.

However, the amino acids (amino acid related compounds) in the living organism include so many kinds. For example, in the inspection items of SRL Inc., 39 kinds of amino acid related compounds are listed as an object for analysis (see, for example, Non-patent literature 2). And, the amino acid concentration in the living organism varies greatly depending on the kind of amino acid, and it is known that there exists concentration difference in about 100 times (double digits) between amino acid with high concentration and amino acid with low concentration. Therefore, on the occasion of performing amino acid analysis using existing mixed standard solution [for example, Amino Acids Mixture Standard Solution, Type AN-II (code numbers: 015-14461, 011-14463), Type B (code numbers: 016-08641, 012-08643), Type H (code numbers: 013-08391, 019-08393), and so on (all are sold from Wako Pure Chemical Industries, Ltd.)], there were a problem of taking time for preparatory work such that depending on the concentration range of each amino acid related compound, dilution of the standard substance or specimen sample is needed.

On the other hand, although a report on the reference standard substance for the amino acids in human plasma has been published (Non-patent Reference 3), since the standard substance in said report was a mixed plasma pool of the plasma obtained from 100 men and women of unspecified number of Americans, the lot-to-lot variation of concentration value could not be avoided. In addition, in the case where the amino acid analysis is carried out using it as a standard solution, since the concentration of each kind of amino acid contained in this standard substance was the average of 100 persons, when the amino acid concentration in a specimen sample exceeds the average value, its concentration would deviate from the range of calibration curve, showing lacked reliability in measurement accuracy. Furthermore, since said standard substance was the one which includes various biological substances other than amino acid, it could not deny the possibility of influence of these substances on the measurement value, and had a problem of employing it as a standard substance for carrying out the quantitative analysis with high degree of accuracy.

Therefore, development of a standard substance that does not need to adjust its concentration depending on the kinds of amino acids to be measured, and by using a solution diluted appropriately from single solution, it can provide a calibration curve which enables to perform quantitative method of various kinds of amino acid in a sample derived from living organism in high accuracy has been desired.

Furthermore, in the quantitative analysis method employing the calibration curve method, there are so-called external standard method and internal standard method, etc., and regarding the internal standard substance, similarly to the case with the external standard substance, quantitative accuracy can be increased by designing the standard substance according to the nature of the specimen sample. In particular, when a mass spectrometer is used as a detector, since the impact of matrix effect in the sample is large, it will be very important to use the internal standards for carrying out measurement with a high degree of accuracy.

Although several researches have been reported on the measurement of amino acid employing this internal standard method (see, for example, Non-patent literature 4 and 5), conventional internal standard substances might sometimes show unfavorable linearity between concentration and signal, and had problems such that if these were used, accuracy of amino acid measurement would be not good. Therefore, development of an internal standard substance which solved such problem has been desired.

CITATION LIST

Patent Literature

Patent literature 1: WO2003/069328

Non-Patent Literature

Non-patent literature 1: B. D. Bennett, E. H. Kimball, M. Gao, R. Osterhout, S. J. Van Dien and J. D. Rabinowitz, Nat. Chem. Biol., 5, 593-599 (2009);
Non-patent literature 2:
http://www.srl.info/srlinfo/kensa_ref_CD/KENSA/SRL6354.htm;
Non-patent literature 3:
http://www.nist.gov/cstl/analytical/organic/metabolitesinserum.cfm:
Non-patent literature 4: Kazutaka Shimbo, Takashi Oonuki, Akihisa Yahashi, Kazuo Hirayama and Hiroshi Miyano, Rapid Commun. Mass Spectrom. 2009; 23: 1483-1492;
Non-patent literature 5: E. A. McGaw, K. W. Phinney and M. S.
Lowenthal. J Chromatogr A. 2010; 1217: 5822-5831.

SUMMARY OF THE INVENTION

Technical Problem

The present invention is made in view of the above described situation, and the problem to be solved is to carry out the quantitative determination of amino acid simply and with high accuracy. More specifically, the purpose is to provide an external standard solution, an external standard substance, an internal standard solution and an internal standard substance, for use in carrying out the quantitative analysis of the amino acids present in plasma simply and with high accuracy, and a method for quantitative method of amino acid in plasma using the same.

Means for Solving the Problem

To solve the above described problem, the present inventors have first determined statistically the concentration distribution of each amino acid in the human plasma which serves as a criteria, by analyzing respective amino acid concentration in human plasma specimens of 6469 specimens. And then, the external standard solution was prepared based on said concentration distribution. As a result, the present inventors have found that said external standard solution, unlike the conventional ones, can determine the amino acid concentration in the specimen sample with high accuracy, because if the calibration curve is made up with the use of the external standard solution and the one diluted appropriately this, the concentration of various kinds of amino acid in the most of specimen will be within the calibration curve used these, and came to complete the present invention. Furthermore, the present inventors have found that, for example, when a liquid chromatography equipped with a mass spectrometer as a detector was used, by using the specific amino acid, which has been labeled with a stable isotope, as an internal standard substance, the relationship between the concentration of internal standard substance and signal became linear, and highly accurate amino acid analysis became possible, and came to complete the present invention.

That is, an external standard solution for use in the analysis of amino acid in plasma of the present invention (hereinafter, sometimes abbreviated simply as an external standard solution of the present invention) is the one which comprises various kinds of amino acids with a concentration balance in the actual plasma, based on the concentration distribution of various amino acid in plasma obtained from specimen data of as many as 6469 specimens, by using relevant standard solution for making a calibration curve of the quantitative analysis of amino acids, a calibration curve having a concentration difference which covers most part of the actual amino acids concentration in plasma from the minimum concentration to the maximum concentration can be produced, as a consequence, it brings about an effect that the amino acids analysis can be performed more simply and with higher accuracy than before. In addition, the external standard solution of the present invention is characterized in that it is suitable for various types of separation analysis measurement methods such as, for example, a liquid chromatographic method, a gas chromatograph method, a supercritical fluid chromatographic method, an electrophoretic method, an inductively-coupled-plasma method, etc. in combination with a mass spectrometric method, and particularly, suitable for use in the separation analysis measurement of various kinds of amino acid by a chromatographic method in combination with mass spectrometry.

That is, in one embodiment of the present invention, the external standard solution for use in the analysis of amino acid in plasma is characterized in that "the external standard solution contains (1) at least one amino acid selected from the following components A, at a concentration of 0.0007 M (mol/L) to 0.49 M per one amino acid, and (2) (i) at least one amino acid selected from the following components B, at a concentration of 0.2 to 0.9 times of the lowest-concentration amino acid among amino acids selected from the components A, per one amino acid, (ii) at least one amino acid selected from the following components C, at a concentration of 0.1 to 0.4 times of the lowest-concentration amino acid among amino acids selected from the components A, besides, when it includes components B, at a concentration of less than 1 time of the lowest-concentration amino acid among amino acids selected from the components B, per one amino acid, or (iii) at least one amino acid selected from the following components D, at a concentration of 0.05 to 0.2 times of the lowest-concentration amino acid among amino acids selected from the components A, besides, when it includes the components B, at a concentration of less than 1 time of the lowest-concentration amino acid among amino acids selected from the components B, and besides, when it includes the components C, at a concentration of less than 1 time of the lowest-concentration amino acid among amino acids selected from the components C, per one amino acid:
[Components A]
valine, glycine, alanine and glutamine;
[Components B]
serine, proline, threonine, taurine, leucine, isoleucine, lysine, histidine, phenylalanine and tyrosine;
[Components C]
asparagine, ornithine, arginine and tryptophan;
[Components D]
glutamic acid, methionine, citrulline and cystine".

In addition, in one embodiment of the present invention, the external standard solution for use in the analysis of amino acid in plasma is characterized in that "the external standard solution contains (1) at least one amino acid selected from the components A, at 0.0007 M to 0.49 M per one amino acid, and (2) at least one amino acid selected from the components B, at a concentration per one amino acid of 0.2 to 0.9 times of the lowest-concentration amino acid among amino acids selected from the components A".

In addition, in one embodiment of the present invention, the external standard solution for use in the analysis of amino acid in plasma is characterized in that "the external standard solution further contains at least one amino acid selected from the components C, in addition to the above described external standard solution, at a concentration of 0.1 to 0.4 times of the lowest-concentration amino acid among amino acids selected from the components A, and at a concentration of less than 1 time of the lowest-concentration amino acid among amino acids selected from the components B, per one amino acid".

Furthermore, in one embodiment of the present invention, the external standard solution for use in the analysis of amino acid in plasma is characterized in that "the external standard solution further contains, in addition to the above described external standard solution, at least one amino acid selected from the components D, at a concentration of 0.05 to 0.2 times of the lowest-concentration amino acid among amino acids selected from the components A, at a concentration of less than 1 time of the lowest-concentration amino acid among amino acids among amino acids selected from the components B, and at a concentration of less than 1 time of the lowest-concentration amino acid among amino acids selected from the components C, per one amino acid".

In addition, in an another embodiment of the present invention, the external standard solution for use in the analysis of amino acid in plasma is characterized in that "the external standard solution includes valine and at least one of leucine, isoleucine, phenylalanine, tyrosine, histidine, tryptophan, and citrulline, wherein 0.0003 M to 0.49 M of valine is contained, and when leucine is included, leucine is contained less than 0.1 to 1 time concentration of valine, and when isoleucine is included, isoleucine is contained 0.05 to 0.7 times concentration of valine, and when phenylalanine is included, phenylalanine is contained less than 0.1 to 0.6 times concentration of valine, and when tyrosine is included, tyrosine is contained 0.1 to 0.7 times concentration of valine, and when histidine is included, histidine is contained 0.1 to 0.8 times concentration of valine, and when tryptophan is included, tryptophan is contained 0.1 to 0.6 times concentration of valine, besides when leucine, isoleucine, phenylalanine, tyrosine or histidine is included, tryptophan is contained less than 1 time concentration of these. When citrulline is included, citrulline is contained 0.01 to 0.3 times concentration of valine, besides when leucine, isoleucine, phenylalanine, tyrosine, histidine or tryptophan is included, citrulline is contained less than 1 time concentration of these Furthermore, in an another embodiment of the present invention, the external standard solution for use in the analysis of amino acid in plasma is characterized in that "the external standard solution includes valine and at least one of leucine and isoleucine, wherein 0.0003 M to 0.49 M of valine is contained, and when leucine is included, leucine is contained less than 0.1 to 1 time concentration of valine, and when isoleucine is included, isoleucine is contained 0.05 to 0.7 times concentration of valine".

And further, in an another embodiment of the present invention, the external standard solution for use in the analysis of amino acid in plasma is characterized in that "the external standard solution further includes at least one of phenylalanine and tyrosine in addition to the above described standard solution, and when phenylalanine is included, phenylalanine is contained 0.1 to 0.6 times concentration of valine, and when tyrosine is included, tyrosine is contained 0.1 to 0.7 times concentration of valine".

Furthermore, in one embodiment of the present invention, the external standard solution for use in the analysis of amino acid in plasma is characterized in that "the external standard solution further includes at least one of histidine and tryptophan in addition to the above described standard solution, and when histidine is included, histidine is contained 0.1 to 0.8 times concentration of valine, and when tryptophan is included, tryptophan is contained 0.1 to 0.6 times concentration of valine, besides when leucine, isoleucine, phenylalanine, tyrosine or histidine is included, tryptophan is contained less than 1 time concentration of these."

And further, in one embodiment of the present invention, the external standard solution for use in the analysis of amino acid in plasma is characterized in that "the external standard solution further includes citrulline in addition to the above described standard solution, wherein citrulline is contained 0.01 to 0.3 times concentration of valine, besides when leucine, isoleucine, phenylalanine, tyrosine, histidine or tryptophan is included, citrulline is contained less than 1 time concentration of these."

That is, unlike the conventional commercially available external standard substance which was prepared by mixing nearly flat concentrations of amino acids, the present invention can provide an external standard solution which is prepared according to the ratio (amino acid balance) of the existing amino acid concentration in actual human plasma. By preparing several to around 10 diluted solutions from said external standard solution and using them, a calibration curve of various kinds of amino acids for use in the quantitative analysis of amino acid in human plasma can be prepared, and by using the external standard solution as a standard solution of the quantitative method of amino acid, the quantitative determination of amino acids in living organism can be analyzed more simply and with higher accuracy as compared with the case with the conventional standard sub stances.

In addition, since an internal standard solution for use in the analysis of amino acid in plasma of the present invention (hereinafter, sometimes abbreviated simply as an internal standard solution of the present invention) shows excellent linearity between concentration and signal, it enables highly accurate determination of amino acids, and besides when it is used in the chromatographic method, since there is almost no difference in the retention time of amino acid between the amino acid employed in the internal standard solution and the amino acid of a measuring object, it makes an effect of enabling the determination.

The internal standard solution of the present invention is characterized in that "the internal standard solution includes proline, glycine, valine, methionine, tryptophan, tyrosine and taurine, which are labeled with one or more of stable isotope."

Furthermore, the internal standard solution of the present invention is characterized in that "the internal standard solution includes proline, glycine, valine, tryptophan, tyrosine, taurine, isoleucine, phenylalanine and asparagine which are labeled with one or more of stable isotope."

And further, the internal standard solution of the present invention is characterized in that "the internal standard solution includes proline, glycine, valine, tryptophan, tyrosine, taurine, isoleucine, phenylalanine, asparagine, ornithine, ethanolamine, glutamic acid, 3-methylhistidine, serine, histidine and arginine which are labeled with one or more of stable isotope."

The present invention is to provide an internal standard solution which makes an effect that, in conformity to the property of amino acid in plasma, for example, in a chromatographic method, there is almost no difference in retention time, and besides, the relationship between concentration and signal is kept linear. If the above described internal standard solution of the present invention is employed for the quantitative method of amino acid, the quantitative determination of amino acid in a living organism can be analyzed simply and with high accuracy.

Further, in another view point of the present invention, the quantitative method of amino acid of the present invention is characterized in that "it employs the above described external standard solution or external standard substance", and that "it employs the above described external standard solution or external standard substance additionally with internal standard solution or internal standard substance", and furthermore that "it employs the above described internal standard solution or internal standard substance." By doing in this way, the quantitative determination of amino acid in plasma can be analyzed simply and with high accuracy. In addition, in the quantitative method of the present invention, it is particularly preferable to measure with a mass spectrometer. Therefore, the quantitative method of amino acid of the present invention can perform quantitative analysis of the amino acid in plasma not only with simple but also with markedly high accuracy, as compared with the case where the conventional external standard substance or/and an internal standard substance are employed.

Effect of the Invention

In the standard solution of the present invention, the concentration distribution of various amino acid in human plasma is determined statistically based on the data analyzed separately as many as 6469 human plasma specimens, and according to it, the concentrations of various kinds of amino acids is set. Therefore, standard error of amino acid in human plasma is very low, and highly accurate measurement is enabled by using said standard solution and appropriate diluted solutions thereof, for use in making a calibration curve for quantitative analysis of the amino acid. In addition, since the conventional standard solution was a mixed solution prepared by mixing amino acids with nearly the same concentration, to make the measurement concentration range of various amino acid entered within the range of calibration curve to be made up thereby, the measurement had to be carried out at very many calibration points. However, in the standard solution of the present invention, since the amino acid concentration has been set up based on the data analyzed a lot of human plasma specimens as above, once a series of operations which dilute this with two or more specific dilution magnifications (preparation of several to ten dilution series) is carried out, the standard solution for calibration curve which is better suited for the various concentrations of analysis object amino acids in plasma can simply be provided. Consequently, the calibration points can be reduced, simple measurement is enabled, and further, highly accurate quantitative analysis is enabled.

In addition, as compared with the conventional internal standard solution of amino acid, the internal standard solution of the present invention enables high accuracy determination of amino acid since the relationship between concentration and signal will become linear if this is used after appropriate dilution. Particularly, when the internal standard solution of the present invention is used in a chromatographic method, a high accuracy determination would be enabled since there is almost no difference in the retention time between an amino acid in the internal standard solution and an amino acid of measuring object.

Furthermore, in the determination method of amino acid in plasma of the present invention, by using the above described external standard solution and the internal standard solution in combination, a quantitative analysis with more high accuracy will be enabled.

Therefore, the present invention is extremely useful in the quantitative analysis of amino acid in plasma.

EMBODIMENTS FOR CARRYING OUT THE INVENTION

The External Standard Solution for Use in the Analysis of Amino Acid in Plasma of the Present Invention (The External Standard Solution of the Present Invention)

The external standard solution of the present invention is the one which is employed in a quantitative analysis method using calibration curve method, and used for so called external standard, specifically, it is a mixed solution which was prepared by mixing plural amino acid products (commercial products) as a standard substance (criteria) in accordance with the ratio of existence concentration of various kinds of amino acid in a biological sample from human as a measuring object, and which is also referred to as an external mixed standard solution.

The amino acid to be analyzed with the use of the external standard solution of the present invention includes, preferably, for example, valine (Val), glycine (Gly), alanine (Ala), glutamine (Glu), serine (Ser), proline (Pro), threonine (Thr), taurine (Tau), leucine (Ler), isoleucine (Ile), lysine (Lys), histidine (His), phenylalanine (Phe), tyrosine (Tyr), asparagine (Asn), ornithine (Orn), arginine (Arg), tryptophan (Trp), glutamic acid (Glu), methionine (Met), citrulline (Cit), cystine (Cys), α-aminobutyric acid (ABA), ethanolamine (EtOHNH$_2$), sarcosine (Sar), γ-aminobutyric acid (GABA), β-aminoisobutiric acid (β-AiBA), hydroxyproline (HyPro), aspartic acid (Asp), α-aminoadipic acid (α-AAA), hydroxylysine (HyLys), 1-methylhistidine (1MeHis), 3-methylhistidine (3MeHis), carnosine (Car), anserine (Ans), and so on; and, valine (Val), glycine (Gly), alanine (Ala), glutamine (Glu), serine (Ser), proline (Pro), threonine (Thr), taurine (Tau), leucine (Ler), isoleucine (Ile), lysine (Lys), histidine (His), phenylalanine (Phe), tyrosine (Tyr), asparagine (Asn), ornithine (Orn), arginine (Arg), tryptophan (Trp), glutamic acid (Glu), methionine (Met), citrulline (Cit), cystine (Cys), and so on are particularly preferable.

The external standard solution of the present invention is the one which includes, although being selected appropriately from the above described amino acids depending on the amino acid to be measured, at least 1 amino acid to be included in the following components A, and at least 1 amino acid included in the following components B to D. Specifically, the one which includes at least 1 amino acid to be included in the components A, and at least 1 amino acid included in the components B is preferable, and the one which further includes at least 1 amino acid included in the components C is more preferable, and the one which further includes at least 1 amino acid included in the components D is further preferable.

[Components A]
  valine, glycine, alanine and glutamine;
[Components B]
  serine, proline, threonine, taurine, leucine, isoleucine, lysine, histidine, phenylalanine and tyrosine;
[Components C]
  asparagine, ornithine, arginine and tryptophan;
[Components D]
  glutamic acid, methionine, citrulline and cystine Among the above described components A, valine is preferable.

Among the above described components B, serine, proline, threonine, leucine, isoleucine, lysine, histidine, phenylalanine and tyrosine are preferable, and leucine, isoleucine, histidine, phenylalanine and tyrosine are more preferable.

Among the above described components C, tryptophan and asparagine are preferable, and tryptophan is more preferable.

Among the above described components D, citrulline and methionine are preferable, and citrulline is more preferable.

It should be noted that the external standard solution of the present invention may include, ethanolamine, sarcosine, γ-aminobutyric acid, β-aminoisobutiric acid, hydroxyproline, aspartic acid, α-aminoadipic acid, hydroxylysine, 1-methylhistidine, 3-methylhistidine, carnosine, anserine or α-aminobutyric acid (hereinafter, abbreviated as components E) as the amino acids other than the above described components A to D.

The components of the above described A to D are the ones classified according to the ratio of existence concentration of amino acids in human plasma, and in the order of components A, components B, components C and components D, the existence concentration of amino acid in human plasma decreases. This grouping was done according to the ratio of the existence concentration of amino acids in human plasma, more specifically, it was done not only according to the ratio of mean existence concentration, but (1) taking the median, the maximum value and the minimum value, etc. of existence concentration into consideration, the amino acid which the maximum value of existence concentration is high is set slightly higher side than the ratio of mean existence concentration, and the amino acid which the minimum value of existence concentration is low is set slightly lower side than the ratio of mean existence concentration, (2) taking the concentration distribution of amino acid into consideration, when the amino acid distributes mostly in higher concentration than the mean existence concentration, it is set slightly higher side than the ratio of mean existence concentration, and when the amino acid distributes mostly in lower concentration than the mean existence concentration, it is set slightly lower side than the ratio of mean existence concentration, or, (3) taking these multiple factors into consideration comprehensively, setting is made, etc. Specifically, for example, in the case of taurine, if it is simply classified according to the mean existence concentration, it will belong to group C, however, because the maximum value of the existence concentration is high, it is preferable to be set not to group C but to high concentration group B. In addition, in the case of isoleucine, if it is simply classified according to the mean existence concentration, it will belong to group C, however, according to the amino acid distribution, frequency of existence in higher concentration than the mean existence concentration is high, therefore, it is preferable to be set not to group C but to high concentration group B.

It should be noted that the existence concentration of amino acid in human plasma may be determined based on the data obtained using many specimens, and the larger number of specimens create the higher accuracy, and therefore a preferable external standard solution which reflects more actual concentration in human plasma will be provided. The concentration ratio of amino acids in the external standard solution of the present invention is calculated using 6469 specimens, and is an excellent one having small standard error. It should be noted that, generally, when n pieces of sample is extracted from a population of standard deviation σ and element count N, the standard error of sample average is estimated by $\sqrt{((N-n)/(N-1))}*(\sigma/\sqrt{n})$, and when N is sufficiently large, estimation is done by $\sigma/\sqrt{n}$. When concentration data are calculated from 6469 specimens, as compared, for example, with the case where concentration data are calculated from 300 specimens, the standard error of sample average will be about 0.22 times, and it turns out that the data with smaller standard error can be obtained.

Specific molar concentration ratio of the amino acid group of the above described components A to D, and preferred molar concentration will be shown as in the following table. It should be note that, in the table, with respect to the molar concentration ratio and the desirable molar concentration ratio when the group A is regarded as 1, in the case where number of the components A is one, it is the molar concentration ratio when the amino acid is regarded as 1; and in the case where the number of the components A is two or more, it represents the molar concentration ratio when the amino acid of the lowest concentration is regarded as 1. In addition, "however, less than 1 time of group B" of the components C represents that when the external standard solution of the present invention includes components B and the components B is one, it will be less than 1 time concentration of the amino acid concentration, when the components B is two or more, it will be less than 1 time concentration of the amino acid of the lowest concentration among them. The "however, less than 1 time of group B, and besides less than 1 time of group C" of the components D represents that when the external standard solution of the present invention includes components B and the components B is one, it will be less than 1 time concentration of the amino acid concentration, and when the components B is two or more, it will be less than 1 time concentration of the amino acid of the lowest concentration among them, and besides when the external standard solution of the present invention includes components C and the components C is one, it will be less than 1 time concentration of the amino acid concentration, and when the components C is two or more, it will be less than 1 time concentration of the amino acid of the lowest concentration among them.

| Group | Molar concentration ratio when group A is regarded as 1 | Preferable molar concentration ratio when group A is regarded as 1 |
|---|---|---|
| A | 1 | 1 |
| B | 0.2-0.9 | 0.4-0.9 |
| C | 0.1-0.4 However, less than 1 time of group B | Less than 0.2-0.4 |
| D | 0.05-0.2 However, less than 1 time of group B, besides, less than 1 time of group C | Less than 0.05-0.2 |

In addition, the concentration of the group A components in the external standard solution of the present invention is usually 0.0007 M to 0.49 M. As for the lower limit thereof, 0.0008 M or higher concentration that is higher than 767.7 µM of glutamine which is the highest mean concentration +2 SD among group A components is preferable, and 0.0013 M or higher concentration that is higher than 1276.9 µM of glutamine which is the highest concentration among group A components is more preferable. As for the upper limit, 0.1 M or less concentration is preferable, and 0.05 M or less concentration is more preferable. Group B to C may be set up so that the molar concentration ratio to group A will be within the ranges of the above described table.

It should be noted that, in the case where the external standard solution of the present invention includes the above described components E, the concentration of the components E may be set up so that, when the external standard solution of the present invention includes components B, it is at less than 1 time concentration of the amino acid with the lowest concentration among them, and besides when the external standard solution of the present invention includes components C, it is at less than 1 time concentration of the amino acid with the lowest concentration among them, and besides, when the external standard solution of the present invention includes components D, it is at less than 1 time concentration of the amino acid with the lowest concentration among them.

As for the external standard solution of the present invention, it is preferable not to make the components A and the components B coexisted with the components D or/and the components E during the time of storage. Specifically, for example, when the one which includes all components A to E is used as an external standard solution of the present invention, it is preferable to store them by dividing into components A, components B and components C, and components D and components E, and at the time of use, the external standard solution comprising all components A to E is prepared by mixing required amount, and then used.

A specific example of preferable amino acid comprised in the external standard solution of the present invention includes, for example, the one which includes valine, and at least any one of leucine, isoleucine, phenylalanine, tyrosine, histidine, tryptophan, and citrulline. Among them, the one which includes valine, and at least any one of leucine and isoleucine is preferable; the one which includes valine, and at least any one of leucine and isoleucine, and at least any one of phenylalanine and tyrosine is more preferable; the one which includes valine, and at least any one of leucine and isoleucine, and at least any one of phenylalanine and tyrosine, and at least any one of histidine and tryptophan is further preferable; the one which includes valine, and at least any one of leucine and isoleucine, and at least any one of phenylalanine and tyrosine, and at least any one of histidine and tryptophan, and citrulline is particularly preferable.

When amino acid is selected from valine, and at least any one of leucine, isoleucine, phenylalanine, tyrosine, histidine, tryptophan, and citrulline, and then an external standard solution are made, respective concentration ratio and desirable concentration ratio are as follows.

| Amino acid | Ratio of molar concentration when valine is regarded as 1 | Preferable ratio of molar concentration when valine is regarded as 1 | More preferable ratio of molar concentration when valine is regarded as 1 |
|---|---|---|---|
| Valine | 1 | 1 | 1 |
| Leucine | 0.1-less than 1 | 0.2-0.9 | 0.4-0.9 |
| Isoleucine | 0.05-0.7 | 0.2-0.7 | 0.4-0.7 |
| Phenylalanine | 0.1-0.6 | 0.2-0.6 | 0.4-0.6 |
| Tyrosine | 0.1-0.7 | 0.2-0.7 | 0.4-0.7 |
| Histidine | 0.1-0.8 | 0.2-0.8 | 0.4-0.8 |
| Tryptophan | 0.1-0.6 However, less than 1 time of leucine, isoleucine, phenylalanine, tyrosine, or histidine | 0.1-0.4 However, less than 1 time of leucine, isoleucine, phenylalanine, tyrosine, or histidine | 0.2-less than 0.4 |
| Citrulline | 0.01-0.3 However, when leucine, isoleucine, phenylalanine, tyrosine, histidine, or tryptophan is included, less than 1 time of them. | 0.05-0.2 However, when leucine, isoleucine, phenylalanine, tyrosine, histidine, or tryptophan is included, less than 1 time of them. | 0.05-less than 0.2 |

In addition, when the external standard solution of the present invention is the one which includes at least valine, besides, includes at least any one of leucine, isoleucine, phenylalanine, tyrosine, histidine, tryptophan, and citrulline, concentration of valine is usually 0.0003 M to 0.49 M. As for the lower limit thereof, 0.0004 M or higher concentration that is higher than 341.4 µM which is average concentration +2 SD of valine is preferable and 0.0005 M or higher concentration that is higher than 469.9 µM which is a maximum concentration of valine is more preferable. As for the upper limit, 0.1 M or lower concentration is preferable, and 0.05 M or lower concentration is more preferable. With respect to other amino acids, the concentration ratios may be set up appropriately in the range used as above described amino acid ratios.

Preparation Method of the External Standard Solution of the Present Invention The external standard solution of the present invention may be prepared by dissolving the above described amino acids in water or buffer solution and the like so that it may provide the above described concentration ratio within the above described concentration range. Such buffer solution includes, specifically, for example, phosphate buffer solution, citrate buffer solution, borate buffer solution, Tris buffer solution such as Tris (hydroxymethyl)aminomethane buffer solution, Good's buffer solution such as N, N-bis (2-hydroxyethyl) glycine (Bicine) buffer solution, 2-[4-(2-hydroxyethyl)-1-pipperadinyl]ethane sulfonic acid (HEPES) buffer solution, 3-morpholinopropane sulfonic acid (MOPS) buffer solution, acetate buffer solution, and carbonate buffer solution, etc.

The external standard solution of the present invention is prepared according to the actual amino acids concentration balance in human plasma samples, by preparing concentration ratio with each amino acid on the basis of a certain specified amino acid concentration. For example, it can be prepared based on the standard value of amino acid concentration shown in Table 3 of the following Example 1 which was obtained from 6469 specimens of human plasma by using conventional standard substance. Specifically, for example, using each amino acid, the external standard substance of 5 steps of concentration 1 to 5 as shown in the following Table 1 may be prepared. It should be noted that, although the concentration 3 is the most close to the average concentration in plasma in the concentrations 1 to 5 shown in the following Table 1, as an external standard solution of the present invention, it is desirable to provide only the concentration 1 of Table 1, and at the time of use, the concentration 2 to 5 of Table 1 is prepared by diluting appropriately this and used.

TABLE 1

| Amino acid (Abbreviation) | Conc. 1 [µM] | Conc. 2 [µM] | Conc. 3 [µM] | Conc. 4 [µM] | Conc. 5 [µM] |
| --- | --- | --- | --- | --- | --- |
| Monoethanolamine (EtOHNH$_2$) | 20 | 10 | 5 | 2 | 1 |
| Glycine (Gly) | 1000 | 500 | 250 | 100 | 50 |
| Sarcosine (Sar) | 20 | 10 | 5 | 2 | 1 |
| Alanine (Ala) | 1000 | 500 | 250 | 100 | 50 |
| γ-Aminobutyric acid (GABA) | 20 | 10 | 5 | 2 | 1 |
| β-Aminoisobutiric acid (β-AiBA) | 20 | 10 | 5 | 2 | 1 |
| α-Aminobutyric acid (α-ABA) | 50 | 25 | 12.5 | 5 | 2.5 |
| Serine (Ser) | 500 | 250 | 125 | 50 | 25 |
| Proline (Pro) | 500 | 250 | 125 | 50 | 25 |
| Valine (Val) | 1000 | 500 | 250 | 100 | 50 |
| Threonine (Thr) | 500 | 250 | 125 | 50 | 25 |
| Taurine (Tau) | 500 | 250 | 125 | 50 | 25 |
| Hydroxyproline (HyPro) | 20 | 10 | 5 | 2 | 1 |
| Leucine (Ler) | 500 | 250 | 125 | 50 | 25 |
| Isoleucine (Ile) | 500 | 250 | 125 | 50 | 25 |
| Asparagine (Asn) | 250 | 125 | 62.5 | 25 | 12.5 |
| Ornithine (Orn) | 250 | 125 | 62.5 | 25 | 12.5 |
| Aspartic acid (Asp) | 20 | 10 | 5 | 2 | 1 |
| Glutamine (Gln) | 1000 | 500 | 250 | 100 | 50 |
| Lysine (Lys) | 500 | 250 | 125 | 50 | 25 |
| Glutamic acid (Glu) | 100 | 50 | 25 | 10 | 5 |
| Methionine (Met) | 100 | 50 | 25 | 10 | 5 |
| Histidine (His) | 500 | 250 | 125 | 50 | 25 |
| α-Aminoadipic acid (α-AAA) | 20 | 10 | 5 | 2 | 1 |
| δ-Hydroxylysine (δ-HyLys) | 20 | 10 | 5 | 2 | 1 |
| Phenylalanine (Phe) | 500 | 250 | 125 | 50 | 25 |
| 1-Methylhistidine (1MeHis) | 20 | 10 | 5 | 2 | 1 |
| 3-Methylhistidine (3MeHis) | 20 | 10 | 5 | 2 | 1 |
| Arginine (Arg) | 250 | 125 | 62.5 | 25 | 12.5 |
| Citrulline (Cit) | 100 | 50 | 25 | 10 | 5 |
| Tyrosine (Tyr) | 500 | 250 | 125 | 50 | 25 |
| Tryptophan (Trp) | 250 | 125 | 62.5 | 25 | 12.5 |
| Carnosine (Car) | 20 | 10 | 5 | 2 | 1 |
| Anserine (Ans) | 20 | 10 | 5 | 2 | 1 |
| Cystine (Cys$_2$) | 100 | 50 | 25 | 10 | 5 |

In addition, in the preparation of the external standard solution of the present invention, as described in the clause of at the time of storage of the standard solution, it is preferable not to make the above described components A and components B coexist with components D or/and components E, and it is preferable to prepare as two separate amino acid mixed-solutions beforehand.

Furthermore, it is more preferable to prepare a final external standard substance by mixing the two amino acid mixed-solutions (1 and 2) prepared beforehand and the amino acids with low stability in solution prepared at the time of use. That is, in another preferable embodiment of the present invention, the external standard substance solution of the present invention is preferable to be prepared as a kit which includes two amino acid mixed-solutions 1 and 2, and the amino acids for preparation at the time of use. In more detail, the amino acid mixed-solution 1 is the one which includes amino acids with relatively low existence concentration in plasma, and specific example of these amino acids are β-AiBA, HyPro, Asp, α-AAA, Sar, δ-HyLys, EtOHNH$_2$, 3MeHis, 1MeHis, Ans, Car, GABA, α-ABA, Cit, Cys$_2$, Glu, and Met, etc. The amino acid mixed-solution 2 is the one which includes amino acids with relatively high existence concentration in plasma, and specific example of such amino acids are Arg, Orn, Ile, Leu, Phe, Pro, Ser, Thr, Tyr, Tau, His, Lys, Gly, Ala, and Val, etc. In addition, the amino acids for preparation at the time of use are the amino acids with relatively low stability in solution, and the specific examples are Asn, Gln, and Trp, etc.

Therefore, the external standard substance of the present invention is prepared by mixing these reagents (that is, the amino acid mixed-solutions 1 and 2, and amino acids for preparation at the time of use). Composition of the prepared preferable external standard substance of the present invention is the one which includes, for example, each 0.02 M of Asp, 3MeHis, EtONH$_2$, 1MeHis, HyPro, Sar, α-AAA, β-AiBA, δ-HyLys, GABA, Ans, Car, etc.; for example, 0.05 M of α-ABA; each 0.1 M of Met, Cit, Glu, Cys$_2$; for example, each 0.25 M of Trp, Orn, Asn, Arg, etc.; for example, each 0.50 M of Phe, Tyr, Tau, His, Ile, Ser, Leu, Thr, Pro, Lys, etc.; and for example, each 1.0 M of Val, Gly, Ala, Gln, etc.

The External Standard Substance for Use in the Analysis of Amino Acid in Plasma of the Present Invention The external standard substance of the present invention may be the one which is made by mixing various kinds of amino acid so as to provide the above described external standard solution of the present invention when a certain amount is dissolved in a certain volume of water or buffer solution, and said amino acids include the same one as described above in the section of external standard solution. In addition, as for said external standard substance, a lyophilized one of the external standard solution of the present invention, or the like is preferable.

The Internal Standard Solution for Use in the Analysis of Amino Acid in Plasma of the Present Invention The internal standard solution of the present invention is so-called internal standard which is used in the quantitative analytical method employing calibration curve method, specifically, taking the ratio of existence concentration of amino acids in a biological sample of measuring object and detection sensitivity, etc. into consideration, mainly, it is a solution obtained by preparing and mixing plural amino acids products as standard substance (criteria), and, it is also referred to as internal mixed standard solution.

Although the internal standard solution of the present invention is characterized by including an amino acid labeled with one or more stable isotope, and it is preferable to be prepared according to the property of the amino acids in a biological sample. That is, for example, in consideration of existence concentration of amino acids, existence of contaminant components, detection sensitivity (detection sensitivity especially to a liquid chromatography-mass spectrometer), degree of peak overlapping between amino acid and internal standards substance, or two or more of these factors in a comprehensive manner, it is preferable to determine kinds of amino acid to be added to an internal standard substance, concentration of the internal standard substance, and the element to be labeled with a stable isotope. For example, with respect to proline which shows high detection sensitivity to the liquid chromatography-mass spectrometer, it is preferable to set the internal standard concentration lower as compared with human plasma balance amino acid concentration, and it is more preferable to make it the lowest concentration in the internal standard solution of the present invention. On the other hand, with respect to taurine which shows low detection sensitivity to the liquid chromatography-mass spectrometer and also has a susceptibility to contaminant components, and cystine which shows low detection sensitivity to the liquid chromatography-mass spectrometer and also shows unfavorable measurement stability due to split of a peak, it is preferable to set the internal standard concentration higher as compared with human plasma balance amino acid concentration, and it is more preferable to set the internal standard concentration of taurine the highest concentration in the internal standard solution of the present invention, and it is further preferable to make the internal standard concentration of taurine the highest concentration and to make the internal standard concentration of cystine high concentration next to taurine.

The amino acid which is labeled with one or more of stable isotope in the internal standard solution of the present invention includes, proline, glycine, valine, methionine, tryptophan, tyrosine, taurine, isoleucine, phenylalanine, asparagine, ornithine, ethanolamine, glutamic acid, 3-methylhistidine, serine, histidine and arginine, sarcosine, alanine, γ-aminobutyric acid, β-aminoisobutiric acid, α-aminobutyric acid, threonine, hydroxyproline, leucine, aspartic acid, glutamine, lysine, α-aminoadipic acid, δ-hydroxylysine, 1-methylhistidine, citrulline, carnosine, anserine, cystine, etc. Among them, the one which includes at least proline, glycine, valine, methionine, tryptophan, tyrosine, and taurine is preferable, and the one which includes at least proline, glycine, valine, methionine, tryptophan, tyrosine, taurine, isoleucine, phenylalanine, and asparagine is more preferable.

The stables isotope in the internal standard solution of the present invention includes, for example, $^2H$, $^{13}C$, $^{15}N$, and $^{18}O$, etc., however, $^{13}C$ and $^{15}N$, etc. are preferable.

The amino acid which is labeled with one or more of stable isotope is preferable to have 3 or more of mass difference relative to unlabeled amino acid. By labeling to an unlabeled amino acid with stable isotope so as to bring about 3 or more of mass differences, the influence due to natural existence ratio of the isotope in the unlabeled object may be reduced, and highly precise analysis can be performed. For example, distribution of the natural isotopes in alanine (molecular formula; $C_3H_7NO_2$, molecular mass 88) are molecular weight 88 (95.8%), 89 (3.74%), 90 (0.34%), and 91 (0.02%), and by making the mass difference into 3 or more, the influence of natural isotopes is avoided mostly.

A specific example of the amino acid which has been labeled with one or more of stable isotopes includes, for example, Pro-U$^{13}C_5$, $^{15}N$; Gly-U$^{13}C_2$, $^{15}N$; Val-U$^{13}C_5$, $^{15}N$; Met-U$^{13}C_5$, $^{15}N$; Trp-U$^{13}C_{11}$, $^{15}N_2$; Tyr-Ring-$^{13}C_6$; Tau-U$^{13}C_2$; Ile-U$^{13}C_6$, $^{15}N$; Phe-U$^{13}C_9$, $^{15}N$; Asn-U$^{13}C_4$, $^{15}N_2$; Orn-U$^{13}C_5$; EtONH$_2$-1, 1, 2, 2-d$_4$; Glu-U$^{13}C_5$; 3MeHis-methyl-d$_3$; Ser-U$^{13}C_3$, $^{15}N$; His-U$^{13}C_6$, $^{15}N3$; and Arg-U$^{15}N_4$.

In the internal standard solution of the present invention, the concentration of the amino acid which has been labeled with one or more of stable isotopes is usually 10 to 300 μM. With respect to the concentration of each amino acid, it is preferable for proline to be made lower concentration than any other amino acids, and it is more preferable for taurine to be made higher concentration than any other amino acids and besides proline is made to be lower concentration than any other amino acids. More specifically, it is preferable to set up the concentration lower in the order of taurine>ethanolamine, glutamic acid, 3-methylhistidine, serine, histidine, arginine, tyrosine>asparagine>isoleucine, ornithine, phenylalanine, tryptophan>glycine, valine, methionine>prorine.

Preparation Method of the Internal Standard Solution of the Present Invention

The internal standard solution of the present invention, according to the property of the amino acids in a biological sample, is prepared by dissolving the above described amino acid which has been labeled with one or more stable isotopes in water or buffer solution and the like so that it may become the above described concentration range. Specifically, it can be prepared based on the standard value of amino acid concentration shown in Table 3 of the following Example. It should be noted that, the above described buffer solution includes the same one as described external standard solution of the present invention.

The Internal Standard Substance for Use in the Analysis of Amino Acid in Plasma of the Present Invention The internal standard substance of the present invention may be the one which is prepared by mixing various kinds of amino acid so as to provide the above described internal standard solution of the present invention when a certain amount is dissolved in a certain volume of water or buffer solution, and said amino acids include the same ones as described above in the section of internal standard solution. In addition, as for such internal standard substance, a lyophilized one of internal standard solution of the present invention or the like is preferable.

The Method for Quantitative Method of Amino Acid in Plasma of the Present Invention Generally, in the method of quantitative analysis using a calibration curve method, there are external standard method (that is, the method using the external standard solution or the external standard substance of the present invention) and internal standard method, and the like. In the quantitative method of the present invention, not only using external standard, if the standard substance which behave similarly to specimen in a specimen (that is, the internal standard solution or the internal standard substance of the present invention) is added to the specimen sample beforehand, it will become possible to increase accuracy of the quantitative method. That is, in the present invention, although it is possible to carry out only by the method using external standard solution or external standard substance, or only by the method using internal standard solution or internal standard substance, a quantitative analysis with more high accuracy can be achieved by employing in combination with both methods.

The quantitative method of amino acid using the external standard solution or the external standard substance in the present invention may be carried out according to the calibration curve method well known per se, however, specifically, for example, 2-times diluted solution, 4-times diluted solution, 10-times diluted solution, and 20-times diluted solution of the external standard solution (or a solution of the external standard substance dissolved in water etc.) of the present invention are prepared, then undiluted solution and these diluted solutions are measured with an appropriate analytic method, and a calibration curve showing the relationship between peak area or peak height and concentration is made up. After that, for example, using human plasma, an amino acid of measuring object is determined, and the concentration is calculated by applying the obtained peak area or peak height to the above described calibration curve, and thus the quantitative method is carried out. The above described analysis method may be the analysis method usually employed in this field, and specifically, for example, liquid chromatography-mass spectrometry (LC-MS), liquid chromatography-mass spectrometry-mass spectrometry (LC-MS-MS), liquid chromatography-fluorescence analysis, liquid chromatography-UV detection, etc. are included, however, among them, LC-MS, LC-MS-MS, etc. using mass spectrometer are preferable. The condition of these analyses may be carried out according to the method well known per se.

It should be noted that, since almost all amino acids have very weak absorption, fluorescence and electrochemical response, it is preferable to carry out analysis after labeling amino group of the amino acid, according to the analytical conditions. In this case, it is preferable to employ a labeling reagent which can exert high selectivity with higher sensitivity, and such labeling reagent includes, specifically, for example, the carbamate compounds described in the patent literature 1, among them, and a 3-aminopyridyl-N-hydroxysuccinimidyl carbamate (APDS) is preferable.

The quantitative method of amino acid using the internal standard solution or the internal standard substance in the present invention may be carried out according to the method well known per se which uses internal standard, however, specifically, for example, the internal standard solution (or a solution of the internal standard substance dissolved in water etc.) is added to human plasma of a specimen, and using it, the amino acid of measuring object and the amino acid labeled with a stable isotope in the internal standard solution are measured by the method described in the quantitative method using the external standard solution, etc. From the obtained peak area or peak height of the amino acid of a measuring object and the peak area or peak height of the amino acid labeled with a stable isotope, the ratio is determined, and after correcting the error caused at the time of preparation and sample injection etc. based on the value, the concentration of the amino acid of a measuring object is calculated.

Hereinafter, the present invention will be explained in more concrete by referring specific Examples, however, the scope of the present invention is not limited thereto in any way.

EXAMPLES

Experimental Example 1

Determination of Plasma Balance Amino Acid Concentration (1) Specimen
As a specimen for determining plasma balance amino acid concentration, 6469 human plasma specimens were used.
(2) External Standard Solution
To commercially available Amino Acids Mixture Standard solution, Type H and Type B (produced by Wako Pure Chemical Industries, Ltd.), various kinds of amino acid listed in the following table were added so that it becomes such concentrations as listed in the following table, and 7 sorts of external standard solutions to add to the above described human plasma specimen were prepared. The concentration in the table shows the concentration after preparation.

TABLE 2

| Amino acid (Abbreviation) | External standard solution (μM) | | | | | | |
|---|---|---|---|---|---|---|---|
| | Conc. 1 | Conc. 2 | Conc. 3 | Conc. 4 | Conc. 5 | Conc. 6 | Conc. 7 |
| EtOHNH$_2$ | 500 | 250 | 100 | 50 | 25 | 10 | 5 |
| Gly | 1000 | 500 | 250 | 100 | 50 | 20 | 10 |
| Sar | 125 | 62.5 | 25 | 12.5 | 6.25 | 2.5 | 1.25 |
| Ala | 1000 | 500 | 250 | 100 | 50 | 20 | 10 |
| GABA | 500 | 250 | 100 | 50 | 25 | 10 | 5 |
| β-AiBA | 500 | 250 | 100 | 50 | 25 | 10 | 5 |
| α-ABA | 500 | 250 | 100 | 50 | 25 | 10 | 5 |
| Ser | 500 | 250 | 100 | 50 | 25 | 10 | 5 |
| Pro | 500 | 250 | 100 | 50 | 25 | 10 | 5 |
| Val | 500 | 250 | 100 | 50 | 25 | 10 | 5 |
| Thr | 500 | 250 | 100 | 50 | 25 | 10 | 5 |
| Tau | 500 | 250 | 100 | 50 | 25 | 10 | 5 |
| HyPro | 500 | 250 | 100 | 50 | 25 | 10 | 5 |
| Leu | 500 | 250 | 100 | 50 | 25 | 10 | 5 |
| Ile | 500 | 250 | 100 | 50 | 25 | 10 | 5 |
| Asn | 500 | 250 | 100 | 50 | 25 | 10 | 5 |
| Orn | 500 | 250 | 100 | 50 | 25 | 10 | 5 |
| Asp | 500 | 250 | 100 | 50 | 25 | 10 | 5 |
| Gln | 1000 | 500 | 250 | 100 | 50 | 20 | 10 |
| Lys | 1000 | 500 | 250 | 100 | 50 | 20 | 10 |

TABLE 2-continued

| Amino acid (Abbreviation) | External standard solution (μM) | | | | | | |
|---|---|---|---|---|---|---|---|
| | Conc. 1 | Conc. 2 | Conc. 3 | Conc. 4 | Conc. 5 | Conc. 6 | Conc. 7 |
| Glu | 500 | 250 | 100 | 50 | 25 | 10 | 5 |
| Met | 500 | 250 | 100 | 50 | 25 | 10 | 5 |
| His | 1000 | 500 | 250 | 100 | 50 | 20 | 10 |
| α-AAA | 500 | 250 | 100 | 50 | 25 | 10 | 5 |
| δ-HyLys | 500 | 250 | 100 | 50 | 25 | 10 | 5 |
| Phe | 500 | 250 | 100 | 50 | 25 | 10 | 5 |
| 1MeHis | 500 | 250 | 100 | 50 | 25 | 10 | 5 |
| 3MeHis | 500 | 250 | 100 | 50 | 25 | 10 | 5 |
| Arg | 1000 | 500 | 250 | 100 | 50 | 20 | 10 |
| Cit | 500 | 250 | 100 | 50 | 25 | 10 | 5 |
| Tyr | 500 | 250 | 100 | 50 | 25 | 10 | 5 |
| Trp | 500 | 250 | 100 | 50 | 25 | 10 | 5 |
| Car | 500 | 250 | 100 | 50 | 25 | 10 | 5 |
| Ans | 500 | 250 | 100 | 50 | 25 | 10 | 5 |
| $Cys_2$ | 500 | 250 | 100 | 50 | 25 | 10 | 5 |

(3) Internal Standard Solution

The following stable isotope-labeled amino acids were obtained from Ajinomoto Co., Inc., Cambridge Isotope Laboratories, Inc., Isotec, Inc., and the internal standard solution containing Gln-$U^{13}C_5$, $^{15}N_2$ (100 μM), Arg-$U^{15}N_4$ (100 μM), His-$U^{15}N_3$ (100 μM) (a part is His-$U^{13}C_6$, $^{15}N_3$ (100 μM)), Glu-$U^{13}C_5$, $^{15}N$ (200 μM), Ser-$U^{13}C_3$, $^{15}N$ (100 μM), Gly-2,2-$d_2$ (50 μM), Ala-3,3,3-$d_3$ (80 μM), Leu-5,5,5-$d_3$ (80 μM), Lys-4,4,5,5-$d_4$ (100 μM), Val-2,3,4,4,4,5,5,5-$d_5$ (25 μM), Met-methyl-$d_3$ (25 μM), Pro-$d_7$ (100 μM), Trp-$U^{13}C_{11}$, $^{15}N_2$ (100 μM), Phe-phenyl-$d_5$ (100 μM), Orn-$U^{13}C_5$ (80 μM) and Cit-4,4,5,5-$d_4$ (100 μM) was prepared.

(4) Pretreatment of Specimen

After 50 μL of the above described specimen was added to 50 μL of the above described internal standard solution and mixed well, 100 μL of acetonitrile was added and further mixed well. After carrying out centrifugal separation of said solution using a high-speed refrigerated micro-centrifugal separator, a supernatant fraction thereof was extracted.

(5) Precolumn Derivatization

Using the obtained supernatant fraction and a labeling reagent (3-aminopyridyl-N-hydroxysuccinimidyl carbamate reagent), precolumn derivatization was carried out. Specifically, to 12 μL of 200 mM borate buffer solution (pH 8.8), 4 μL of the supernatant fraction was added and mixed well, and further, 4 μL of 3-aminopyridyl-N-hydroxysuccinimidyl carbamate reagent (the one which was prepared by dissolving 20 mg of the reagent in 1 mL of acetonitrile) was added and mixed well, then warmed at 55° C. for 5 minutes. Next, to said solution, 60 μL of 25 mM formic acid aqueous ammonia solution (pH 6.0) and 20 μL of 0.1% aqueous formic acid were added and mixed well, and used it as a sample for analysis of high performance liquid chromatography-mass spectrometry.

(6) Analysis with High Performance Liquid Chromatography-Mass Spectrometry Aystem Analysis was carried out on the following conditions:

High performance liquid chromatography: L-2100 series (Hitachi High-Technologies);

Analytical column: Wakosil-II 3C8-100HG (Wako Pure Chemical Industries);

Guard column: Wakosil-II 3C8-100HG (Wako Pure Chemical Industries);

Mobile phases: Mobile phases A: 25 mM formic acid (pH was adjusted to 6.0 with aqueous ammonia);

Mobile phases B: Acetonitrile/water (6:4 (v/v));

Column temperature: 40° C.;

Sample injection volume: 5 μL;

Mass spectrometer: Thermo Scientific Surveyor MSQ Plus (Thermo Fisher Scientific);

Monitor ion:

$EtONH_2$: 182, Gly: 196, Ala: 210, Sar: 210, GABA: 224, β-AiBA: 224, α-ABA: 224, Ser: 226, Pro: 236, Val: 238, Thr: 240, Tau: 246, HyPro: 252, Ile: 252, Leu: 252, Asn: 253, Asp: 254, Gln: 267, Glu: 268, Met: 270, His: 276, α-AAA: 282, Phe: 286, 1MeHis: 290, 3MeHis: 290, Arg: 295, Cit: 296, Tyr: 302, Trp: 325, Car: 347, Ans: 361, Orn: 373, Lys: 387, δ-HyLys: 403, $Cys_2$: 481

(7) Preparation of Calibration Curve

As for the external standard solution, 5 points or more among 7 points of the concentrations 1 to 7 in Table 2 [the point which deviate from a range of ±15% accuracy (lower limit was ±20%) was excluded] was used, not passing the point of origin, but 1/x was used for weighting.

From the above, the amino acid concentration (plasma balance amino acid concentrations) of 6469 specimens were calculated by applying the result of high performance liquid chromatography-mass spectrometry system to the calibration curve. The average concentration, the maximum concentration, the minimum concentration, and standard deviation thereof are shown in the following Table 3. In addition, the graph thereof is shown in the FIGURE.

TABLE 3

| Amino acid (Abbreviation) | Average conc. [μM] | Maximum conc. [μM] | Minimum conc. [μM] | Average conc. + 2SD (Standard deviation) [μM] | Average conc. − 2SD (Standard deviation) [μM] |
|---|---|---|---|---|---|
| $EtOHNH_2$ | 7.2 | 21.6 | 2.0 | 10.6 | 3.7 |
| Gly | 235.7 | 714.1 | 97.3 | 350.9 | 120.5 |
| Sar | 1.8 | 9.3 | 0 | 4.1 | −0.4 |
| Ala | 374.7 | 881.7 | 122.6 | 548.3 | 201.1 |
| GABA | 0.1 | 4.5 | 0 | 0.6 | −0.5 |
| β-AiBA | 1.7 | 89.0 | 0 | 5.3 | −1.9 |
| α-ABA | 18.4 | 57.2 | 3.5 | 29.1 | 7.7 |
| Ser | 112.1 | 237.7 | 31.1 | 154.4 | 69.8 |
| Pro | 147.9 | 905.0 | 58.6 | 236.5 | 59.2 |
| Val | 245.6 | 469.9 | 90.3 | 341.4 | 149.7 |
| Thr | 106.5 | 278.4 | 41.0 | 154.6 | 58.5 |
| Tau | 52.1 | 375.4 | 15.7 | 87.5 | 16.6 |
| HyPro | 12.4 | 113.3 | 0 | 25.4 | −0.5 |
| Leu | 120.3 | 361.1 | 34.6 | 173.3 | 67.3 |
| Ile | 64.7 | 177.5 | 18.2 | 97.5 | 32.0 |
| Asn | 42.7 | 106.3 | 17.7 | 58.0 | 27.5 |
| Orn | 56.8 | 190.9 | 13.8 | 89.6 | 24.0 |
| Asp | 4.3 | 58.0 | 0 | 16.9 | −8.2 |
| Gln | 587.8 | 1276.9 | 223.6 | 767.7 | 407.9 |
| Lys | 207.1 | 426.4 | 83.6 | 283.9 | 130.4 |
| Glu | 35.5 | 133.8 | 0 | 69.8 | 1.2 |
| Met | 27.2 | 166.0 | 10.6 | 39.0 | 15.4 |
| His | 77.4 | 223.2 | 26.1 | 106.9 | 47.8 |
| α-AAA | 0.2 | 24.5 | 0 | 2.2 | −1.8 |
| δ-HyLys | 0 | 11.2 | 0 | 0.4 | −0.4 |
| Phe | 63.7 | 157.0 | 29.3 | 87.0 | 40.4 |
| 1MeHis | 5.1 | 100.7 | 0 | 17.4 | −7.2 |
| 3MeHis | 5 | 43.4 | 0 | 8.8 | 1.3 |
| Arg | 95.4 | 226.3 | 27.2 | 139.4 | 51.3 |
| Cit | 21.4 | 94.0 | 6.7 | 34.0 | 8.7 |
| Tyr | 72.2 | 169.3 | 14.2 | 104.2 | 40.2 |
| Trp | 62.7 | 139.9 | 13.4 | 87.4 | 38.0 |
| Car | 0 | 3.7 | 0 | 0.5 | −0.4 |
| Ans | 0.1 | 4.2 | 0 | 0.8 | −0.7 |
| $Cys_2$ | 30.4 | 95.0 | 0 | 50.8 | 10.0 |

Figure 1:
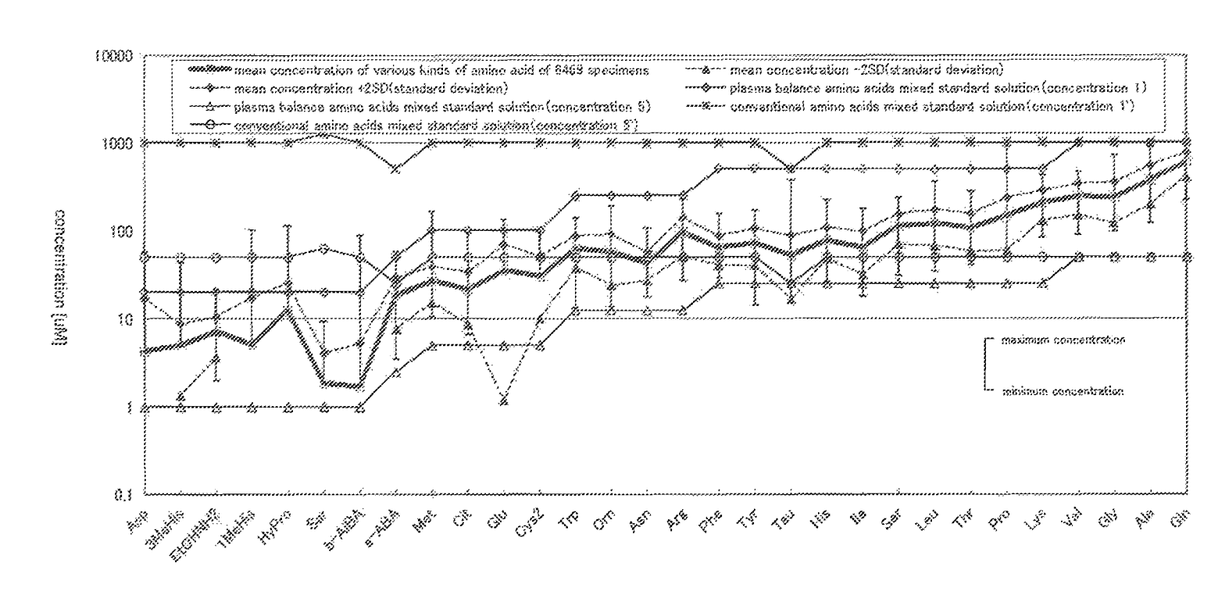
The FIGURE is a graph showing mean concentration, maximum concentration, minimum concentration, mean concentration +2 SD (standard deviation) and mean concentration −2 SD (standard deviation) of various kinds of amino acid which were determined in Example 1, concentration distributions of the external standard solution of the present invention (concentration 1 and concentration 5) which were prepared in Example 1, and the conventional mixed amino acids standard solution (concentration 1' and concentration 5') prepared in Comparative Example 1.

Example 1: Preparation of the External Standard Solution (a Solution Comprising Plasma Balance Amino Acids Mixed Substance) of the Present Invention Using various kinds of amino acid products (EtONH$_2$, Gly, Sar, Ala, GABA, β-AiBA, α-ABA, Ser, Pro, Val, Thr, Tau, Hypro, Leu, Ile, Orn, Asp, Lys, Glu, Met, His, α-AAA, δ-HyLys, Phe, 1MeHis, 3MeHis, Arg, Cit, Tyr, Car, Ans, and Cys$_2$ were all produced by Wako Pure Chemical Industries, Ltd.), and by taking the amino acid concentration ratio in plasma [that is, human plasma balance amino acid concentration determined in Comparative Example 1 (refer to Table 3 and FIG. 1)] and the stability of the amino acid, into account, the following amino acid mixed solutions 1 and 2 were prepared.

Amino Acid Mixed Solution 1:

An aqueous solution containing each 200 μM of β-AiBA, HyPro, Asp, α-AAA, Sar, δ-HyLys, EtONH$_2$, 3MeHis, 1MeHis, Ans, Car and GABA; 500 μM of α-ABA; and each 1000 μM of Cit, Cys$_2$, Glu and Met.

Amino Acid Mixed Solution 2:

An aqueous solution comprising each 2500 μM of Arg and Orn; each 5000 μM of Ile, Leu, Phe, Pro, Ser, Thr, Tyr, Tau, His, and Lys; and each 10000 μM of Gly, Ala, and Val.

Subsequently, the amino acid mixed solutions 1 and 2, and Asn, Gln, and Trp (produced by SIGMA Co., Ltd.), which have been prepared at the time of use were mixed, and an external standard solution (plasma balance amino acids mixed standard solution), which amino acids was mixed with a composition shown below, was prepared.

It includes each 20 μM of Asp, 3MeHis, EtONH$_2$, 1MeHis, HyPro, Sar, α-AAA, β-AiBA, δ-HyLys, GABA, Ans, and Car; 50 μM of α-ABA; each 100 μM of Met, Cit, Glu, and Cys$_2$; each 250 μM of Trp, Orn, Asn, and Arg; each 500 μM of Phe, Tyr, Tau, His, Ile, Ser, Leu, Thr, Pro, and Lys; and each 1000 μM of Val, Gly, Ala, and Gln.

The following Table 4 shows the contents of the external standard solution (plasma balance amino acids mixed standard solution) of the present invention prepared from the above described results. In addition, graphs about concentration 1 and concentration 5 are shown in the FIGURE.

Comparative Example 1: The External Standard Solution as a Conventional Product

As a control for the external standard solution of the present invention in Example 1, an amino acids mixed standard solution was prepared using Amino Acids Mixture Standard solution, Type B (produced by Wako Pure Chemical Industries, Ltd.) and Amino Acids Mixture Standard solution, Type ANII (produced by Wako Pure Chemical Industries, Ltd.) in place of using the above described amino acids mixed solutions 1 and 2.

In the following Table 4, the contents of said amino acids mixed standard solution is shown together with the above described external standard solution of the present invention. In addition, graphs for concentration V and concentration 5' are shown in the FIGURE.

TABLE 4

| Amino acid (Abbrev.) | Example 1 External standard solution (Plasma balance amino acids mixed standard solution) | | | | | Comparative Example 1 External standard solution (Conventional amino acids mixed standard solution) | | | | |
|---|---|---|---|---|---|---|---|---|---|---|
| | Conc. 1 [μM] | Conc. 2 [μM] | Conc. 3 [μM] | Conc. 4 [μM] | Conc. 5 [μM] | Conc. 1' [μM] | Conc. 2' [μM] | Conc. 3' [μM] | Conc. 4' [μM] | Conc. 5' [μM] |
| EtOHNH$_2$ | 20 | 10 | 5 | 2 | 1 | 1000 | 500 | 250 | 100 | 50 |
| Gly | 1000 | 500 | 250 | 100 | 50 | 1000 | 500 | 250 | 100 | 50 |
| Sar | 20 | 10 | 5 | 2 | 1 | 2500 | 1250 | 625 | 250 | 125 |
| Ala | 1000 | 500 | 250 | 100 | 50 | 1000 | 500 | 250 | 100 | 50 |
| GABA | 20 | 10 | 5 | 2 | 1 | 1000 | 500 | 250 | 100 | 50 |
| β-AiBA | 20 | 10 | 5 | 2 | 1 | 1000 | 500 | 250 | 100 | 50 |
| α-ABA | 50 | 25 | 12.5 | 5 | 2.5 | 500 | 250 | 125 | 50 | 25 |
| Ser | 500 | 250 | 125 | 50 | 25 | 1000 | 500 | 250 | 100 | 50 |
| Pro | 500 | 250 | 125 | 50 | 25 | 1000 | 500 | 250 | 100 | 50 |
| Val | 1000 | 500 | 250 | 100 | 50 | 1000 | 500 | 250 | 100 | 50 |
| Thr | 500 | 250 | 125 | 50 | 25 | 1000 | 500 | 250 | 100 | 50 |
| Tau | 500 | 250 | 125 | 50 | 25 | 500 | 250 | 125 | 50 | 25 |
| HyPro | 20 | 10 | 5 | 2 | 1 | 1000 | 500 | 250 | 100 | 50 |
| Leu | 500 | 250 | 125 | 50 | 25 | 1000 | 500 | 250 | 100 | 50 |
| Ile | 500 | 250 | 125 | 50 | 25 | 1000 | 500 | 250 | 100 | 50 |
| Asn | 250 | 125 | 62.5 | 25 | 12.5 | 1000 | 500 | 250 | 100 | 50 |
| Orn | 250 | 125 | 62.5 | 25 | 12.5 | 1000 | 500 | 250 | 100 | 50 |
| Asp | 20 | 10 | 5 | 2 | 1 | 1000 | 500 | 250 | 100 | 50 |
| Gln | 1000 | 500 | 250 | 100 | 50 | 1000 | 500 | 250 | 100 | 50 |
| Lys | 500 | 250 | 125 | 50 | 25 | 1000 | 500 | 250 | 100 | 50 |
| Glu | 100 | 50 | 25 | 10 | 5 | 1000 | 500 | 250 | 100 | 50 |
| Met | 100 | 50 | 25 | 10 | 5 | 1000 | 500 | 250 | 100 | 50 |
| His | 500 | 250 | 125 | 50 | 25 | 1000 | 500 | 250 | 100 | 50 |
| α-AAA | 20 | 10 | 5 | 2 | 1 | 500 | 250 | 125 | 50 | 25 |
| δ-HyLys | 20 | 10 | 5 | 2 | 1 | 1000 | 500 | 250 | 100 | 50 |
| Phe | 500 | 250 | 125 | 50 | 25 | 1000 | 500 | 250 | 100 | 50 |
| 1MeHis | 20 | 10 | 5 | 2 | 1 | 1000 | 500 | 250 | 100 | 50 |
| 3MeHis | 20 | 10 | 5 | 2 | 1 | 1000 | 500 | 250 | 100 | 50 |
| Arg | 250 | 125 | 62.5 | 25 | 12.5 | 1000 | 500 | 250 | 100 | 50 |
| Cit | 100 | 50 | 25 | 10 | 5 | 1000 | 500 | 250 | 100 | 50 |
| Tyr | 500 | 250 | 125 | 50 | 25 | 1000 | 500 | 250 | 100 | 50 |
| Trp | 250 | 125 | 62.5 | 25 | 12.5 | 1000 | 500 | 250 | 100 | 50 |

TABLE 4-continued

| Amino acid (Abbrev.) | Example 1 External standard solution (Plasma balance amino acids mixed standard solution) | | | | | Comparative Example 1 External standard solution (Conventional amino acids mixed standard solution) | | | | |
| --- | --- | --- | --- | --- | --- | --- | --- | --- | --- | --- |
| | Conc. 1 [μM] | Conc. 2 [μM] | Conc. 3 [μM] | Conc. 4 [μM] | Conc. 5 [μM] | Conc. 1' [μM] | Conc. 2' [μM] | Conc. 3' [μM] | Conc. 4' [μM] | Conc. 5' [μM] |
| Car | 20 | 10 | 5 | 2 | 1 | 1000 | 500 | 250 | 100 | 50 |
| Ans | 20 | 10 | 5 | 2 | 1 | 1000 | 500 | 250 | 100 | 50 |
| Cys$_2$ | 100 | 50 | 25 | 10 | 5 | 1000 | 500 | 250 | 100 | 50 |

Example 2: Preparation of the Internal Standard Solution of the Present Invention The following stable isotope-labeled amino acids were obtained from Ajinomoto Co., Inc., Cambridge Isotope Laboratories, Inc. and Isotec, Inc., and the internal standard solution containing Gln-U$^{13}$C$_5$, $^{15}$N$_2$ (100 μM), Arg-U$^{15}$N$_4$ (100 μM), His-U$^{13}$C$_6$, $^{15}$N$_3$ (100 μM), Glu-U$^{13}$C$_5$, $^{15}$N (100 μM), Ser-U$^{13}$C$_3$, $^{15}$N (100 μM), Gly-U$^{13}$C$_2$, $^{15}$N (50 μM), Ala-3,3,3-d$_3$ (100 μM), Leu-5,5,5-d$_3$ (80 μM), Lys-U$^{13}$C$_6$, $^{15}$N$_2$ (130 μM), Val-U$^{13}$C$_5$, $^{15}$N (50 μM), Met-U$^{13}$C$_5$, $^{15}$N (50 μM), Pro-U$^{13}$C$_5$, $^{15}$N (25 μM), Trp-U$^{13}$C$_{11}$, $^{15}$N$_2$ (80 μM), Phe-U$^{13}$C$_9$, $^{15}$N (80 μM), Orn-U$^{13}$C$_5$ (80 μM), Cit-4,4,5,5-d$_4$ (100 μM), Thr-U$^{13}$C$_4$ (100 μM), Tyr-Ring-$^{13}$C$_6$ (100 μM), Tau-U$^{13}$C$_2$ (250 μM), Ile-U$^{13}$C$_6$, $^{15}$N (80 μM), Asn-U$^{13}$C$_4$, $^{15}$N$_2$ (90 μM), 3MeHis-methyl-d$_3$ (100 μM), Asp-2,3,3-d$_3$ (100 μM), Cys2-3,3,3',3'-d$_4$ (200 μM) and EtONH$_2$-1,1,2,2-d$_4$ (100 μM) was prepared.

As a control, the internal standard solution described in Non-patent Literature 4 was adjusted, and it was used as an internal standard solution (the conventional internal standard solution) as a comparative example for Example 2.

The following table 5 shows the internal standard solutions for various kinds of amino acid when the concentration of various kinds of amino acid in human plasma are measured using the above described internal standard solution (the internal standard solution of the present invention) or the internal standard solution (the conventional internal standard solution) of Comparative Example. In the Table, gray colored frames indicate the amino acids for which the stable isotope of itself is not employed as the internal standard solution. As for the amino acids in gray colored frames, in consideration of the nearness of retention time with the amino acids which are not labeled with stables isotope, the physical properties of a compound, the result of an addition recovery examination, etc., the most suitable ones were selected from various kinds of amino acid which have been labeled with stable isotope.

TABLE 5

| Amino acid (Abbrev.) | Example 2 Internal standard solution (Internal standard solution of the present invention) | Conc. [μM] | Comparative Example Internal standard solution (Conventional internal standard solution) | Conc. [μM] |
| --- | --- | --- | --- | --- |
| EtOHNH$_2$ | EtONH$_2$-1,1,2,2-d$_4$ | 100 | | |
| Gly | Gly-U$^{13}$C$_2$,$^{15}$N | 50 | Gly-2,2-d$_3$ | 50 |
| Sar* | Glu-U$^{13}$C$_5$,$^{15}$N | 100 | | |
| Ala | Ala-3,3,3-d$_3$ | 100 | Ala-3,3,3-d$_3$ | 80 |
| GABA* | 3MeHis-methyl-d$_3$ | 100 | | |
| β-AiBA* | EtONH2-1,1,2,2-d$_4$ | 100 | | |
| α-ABA* | 3MeHis-methyl-d$_3$ | 100 | | |
| Ser | Ser-U$^{13}$C$_3$, $^{15}$N | 100 | Ser-U$^{13}$C$_3$, $^{15}$N | 100 |
| Pro | Pro-U$^{13}$C$_5$, $^{15}$N | 25 | Pro-d$_7$ | 100 |
| Val | Val-U$^{13}$C$_5$, $^{15}$N | 50 | Val-2,3,4,4,4,5,5,5-d$_8$ | 25 |
| Thr | Thr-U$^{13}$C$_4$ | 100 | Ser-U$^{13}$C$_3$, $^{15}$N | 100 |
| Tau | Tau-U$^{13}$C$_4$ | 100 | Ala-3,3,3-d$_3$ | 80 |
| Hypro* | Glu-U$^{13}$C$_5$, $^{15}$N | 100 | | |
| Leu | Leu-5,5,5-d$_3$ | 80 | Leu-5,5,5-d$_3$ | 80 |
| Ile | Ile-U$^{13}$C$_6$, $^{15}$N | 80 | Leu-5,5,5-d$_3$ | 80 |
| Asn | Asn-U$^{13}$C$_6$, $^{15}$N$_2$ | 90 | Ser-U$^{13}$C$_3$, $^{15}$N | 100 |
| Orn | Orn-U$^{13}$C$_5$ | 80 | Lys-4,4,5,5-d$_4$ | 100 |
| Asp | Asp-2,3,3-d$_3$ | 100 | Glu-U$^{13}$C$_5$, $^{15}$N | 200 |
| Gln | Gln-U$^{13}$C$_5$, $^{15}$N$_2$ | 100 | Gln-U$^{13}$C$_5$, $^{15}$N$_2$ | 100 |
| Lys | Lys-U$^{13}$C$_6$, $^{15}$N$_2$ | 130 | Lys-4,4,5,5-d4 | 100 |
| Glu | Glu-U$^{13}$C$_5$, $^{15}$N | 100 | Glu-U$^{13}$C$_5$, $^{15}$N | 200 |
| Met | Met-U$^{13}$C$_5$, $^{15}$N | 50 | Met-methyl-d$_3$ | 25 |
| His | His-U$^{13}$C$_6$, $^{15}$N$_3$ | 100 | His-U$^{15}$N$_3$ | 100 |
| α-AAA* | Ser-U$^{13}$C$_3$, $^{15}$N | 100 | | |
| δ-HyLys* | Orn-U$^{13}$C$_5$ | 80 | | |
| Phe | Phe-U$^{13}$C$_9$, $^{15}$N | 80 | Leu-5,5,5-d$_3$ | 80 |
| 1MeHis* | His-U$^{13}$C$_6$, $^{15}$N$_3$ | 100 | | |
| 3MeHis* | 3MeHis-methyl-d$_3$ | 100 | | |
| Arg | Arg-U$^{15}$N$_4$ | 100 | Arg-U$^{15}$N$_4$ | 100 |
| Cit | Cit-4,4,5,5-d$_4$ | 100 | Pro-d$_7$ | 100 |
| Tyr | Tyr-Ring-$^{13}$C$_6$ | 100 | Pro-d$_7$ | 100 |
| Trp | Trp-U$^{13}$C$_{11}$, $^{15}$N$_2$ | 80 | Leu-5,5,5-d$_3$ | 80 |
| Car | Arg-U$^{15}$N$_4$ | 100 | | |
| Ans | EtONH$_2$-1,1,2,2-d$_4$ | 100 | | |
| Cys$_2$ | Cys$_2$-3,3,3',3'-d$_4$ | 200 | | |

Example 3: Quantitative Analysis Using External Standard Solution of the Present Invention (1) Preparation of Biological Sample As a biological sample, the blood was collected from 5 healthy volunteers, and plasma was combined after plasma separation and used it as pooled plasma.

(2) Preparation of Known Concentration Amino Acid Addition Plasma and Control Plasma A specimen which was prepared by mixing the obtained pool plasma with a mixed solution of known concentration amino acids described in the following Table 6 by 1:1 was used as known concentration amino acid addition plasma, and a specimen which was prepared by mixing the obtained pool plasma with waters by 1:1 was used as control plasma.

(3) Pretreatment of Specimen

To 50 μL of the above described known concentration amino acid addition plasma or the control plasma, 50 μL of the internal standard solution of Example 2 was added and mixed well, then 100 μL of acetonitrile was added to it and mixed well.

Subsequently, after carrying out centrifugal separation with a high-speed refrigerated micro-centrifugal separator, obtained supernatant fraction was used for analysis.
(4) Precolumn Derivatization Using the obtained supernatant fraction and a labeling reagent (3-aminopyridyl-N-hydroxysuccinimidyl carbamate reagent), precolumn derivatization was carried out. Specifically, to 60 µL of 200 mM borate buffer solution (pH 8.8), 20 µL of the supernatant fraction was added and mixed well. Further, 20 µL of 3-aminopyridyl-N-hydroxysuccinimidyl carbamate reagent (the one which was prepared by dissolving 20 mg of the reagent in 1 mL of acetonitrile) was added and mixed well, then warmed at 55° C. for 10 minutes. Subsequently, after said solution was kept standing to cool at room temperature, 100 µL of 0.1% aqueous formic acid solution was added and mixed well, and used it as a sample for analysis of high performance liquid chromatography-mass spectrometry.
(5) Analysis with High Performance Liquid Chromatography-Mass Spectrometry System Analysis was carried out on the following conditions:
High performance liquid chromatography: 10Avp series (Shimazu Corporation);
Analytical column: Inartsil C8-3 (GL Science Inc.);
Guard column: Inartsil ODS-3 (GL Science Inc.);
Mobile phases: Mobile phases A: 25 mM formic acid (pH was adjusted to 6.0 with aqueous ammonia);
Mobile phases B: Acetonitrile/water (6:4 (v/v));
Column temperature: 40° C.;
Sample injection volume: 3 µL;
Mass spectrometer: API3000 LC/MS/MS (AB SCIEX);
Monitor ion (Q1/Q3):
EtONH$_2$: 182/121, Gly: 196/121, Ala: 210/121, Sar: 210/121, GABA: 224/121, β-AiBA: 224/121, α-ABA: 224/121, Ser: 226/121, Pro: 236/121, Val: 238/121, Thr: 240/121, Tau: 246/121, HyPro: 252/121, Ile: 252/121, Leu: 252/121, Asn: 253/121, Asp: 254/121, Gln: 267/121, Glu: 268/121, Met: 270/121, His: 276/121, α-AAA: 282/121, Phe: 286/121, 1MeHis: 290/121, 3MeHis: 290/121, Arg: 295/121, Cit: 296/121, Tyr: 302/121, Trp: 325/121, Car: 347/121, Ans: 361/121, Orn: 373/121, Lys: 387/121, δ-HyLys: 403/121, Cys$_2$: 481/121.
(6) Preparation of Calibration Curve Using the external standard solution of Example 1, as is the case with the above described known concentration amino acid addition plasma, derivatization treatment of the above described (4) was carried out, and analysis of (5) was performed. From the results of analysis, a calibration curve which has 20-times concentration difference between upper limit concentration and lower limit concentration was prepared. As for the external standard solution, 5 points of the concentration 1 to 5 in Table 4 (plasma balance amino acids mixed standard solutions) was used, not passing the point of origin, but 1/x was used for weighting.
(7) Addition and Recovery of Amino Acid to Plasma From the measurement results of the known concentration amino acids addition plasma, addition and recovery rate was determined. The addition and recovery rate was calculated as follows:

Addition and recovery rate={(amino acid concentration in known concentration amino acids addition plasma)−(amino acid concentration in control plasma)}×2/added known concentration amino acid (%)

It should be noted that each concentration was calculated after determining peak area ratio {(peak area of each component)/(peak area of internal standard solution)}, and using the above described calibration curve. The results are shown in Table 6. Here, the addition and recovery rate of Example is the value calculated based on the calibration curve which was made up using the external standard solution (plasma balance amino acid acids mixed standard solution) of Example 1.

Comparative Example 2: Quantitative Analysis Using the External Standard Solution of Comparative Example 1

In (6) of Example 3, addition and recovery rate when the amino acids were added to human plasma was determined by the same method as Example 3 except for using 5 points of concentration 1' to 5' (conventional amino acids mixed standard solution) of Table 4. The results are shown in Table 6 in conjunction with the results of Example 3. In the Table, the addition and recovery rate of Comparative Example is the value calculated based on the calibration curve made up using the external standard solution (conventional amino acids mixed standard solution) prepared as a control.

TABLE 6

| Amino acid (Abbrev.) | Addition concentration (known concentration amino acids mixed solution) [µM] | Addition and recovery rate [%] Example 3 | Addition and recovery rate [%] Comparative Example 2 |
|---|---|---|---|
| EtOHNH$_2$ | 10 | 102% | 35% |
| Gly | 500 | 106% | 107% |
| Sar | 10 | 111% | 0% |
| Ala | 500 | 98% | 99% |
| GABA | 10 | 94% | 0% |
| β-AiBA | 10 | 102% | 28% |
| α-ABA | 25 | 105% | 107% |
| Ser | 250 | 99% | 87% |
| Pro | 250 | 100% | 118% |
| Val | 500 | 100% | 99% |
| Thr | 250 | 97% | 84% |
| Tau | 250 | 98% | 83% |
| HyPro | 10 | 102% | 98% |
| Leu | 250 | 98% | 96% |
| Ile | 250 | 101% | 100% |
| Asn | 125 | 95% | 92% |
| Orn | 125 | 102% | 95% |
| Asp | 10 | 81% | 48% |
| Gln | 1000 | 100% | 97% |
| Lys | 250 | 103% | 101% |
| Glu | 50 | 107% | 108% |
| Met | 50 | 103% | 109% |
| His | 250 | 93% | 85% |
| α-AAA | 10 | 101% | 51% |
| δ-HyLys | 10 | 101% | 392% |
| Phe | 250 | 102% | 104% |
| 1MeHis | 10 | 95% | 66% |
| 3MeHis | 10 | 100% | 7% |
| Arg | 125 | 99% | 91% |
| Cit | 50 | 103% | 110% |
| Tyr | 250 | 97% | 106% |
| Trp | 125 | 93% | 102% |
| Car | 10 | 100% | 44% |
| Ans | 10 | 92% | 0% |
| Cys$_2$ | 50 | 80% | 65% |

When the external standard solution (plasma balance amino acids mixed standard solution) of the present invention prepared in Example 1 was employed, the recovery rate of 35 kinds of compound employed as a standard product was 80 to 111%, while when the external standard solution (the conventional amino acids mixed standard solution) of Comparative Example was employed, it was 0 to 392%. That is, using the external standard solution (the conventional amino acids mixed standard solution) of Comparative Example, in the case where the calibration curve was made up using 5 calibration points in the range where lower limit concentration gave 20 time dilution of the upper limit concentration, the result was lacking in accuracy because there were many compounds whose quantitative values is outside the range of the calibration curve. In other words, it turned out that in order to make various kinds of amino acid positioned within the limits of a calibration curve using the external standard solution of Comparative Example (conventional amino acids mixed standard solution), it is necessary to increase the dilution magnification of the lower limit concentration relative to the upper limit concentration, and besides, to increase the number of calibration points (for example, at 1000 times dilution concentration, and 10 calibration points).

On the other hand, it turned out that when a calibration curve was made up using the external standard solution (plasma balance amino acids mixed standard solution) of the present invention obtained in Example 1, even if it had a range where the minimum concentration was given by 20 time dilution of the maximum concentration, and even if calibration point was 5 points, the concentration of various kinds of amino acid can be measured with high accuracy because the concentration of various kinds of amino acid enters within the range of calibration curve. Therefore, it turned out that the external standard solution (plasma balance amino acids mixed standard solution) of the present invention is very useful in determination of amino acids in a biological sample.

Example 4: Quantitative Analysis of Amino Acids in the External Standard Solution Using Internal Standard Solution of the Present Invention (1) An Internal Standard Solution and an External Standard Solution of the Present Invention The internal standard solution (Example 2 in Table 5) of the present invention prepared in Example 2 was employed as an internal standard. In addition, as a comparative example, the conventional internal standard solution (Comparative Example in Table 5) prepared in Example 2 was used as an internal standard.

In addition, the external standard solution (plasma balance amino acids mixed standard solution) of the present invention of the concentration 1 in Table 4 obtained in Example 1 was subjected to serial dilution in turn to give 5/4-times, 5/3-times, 2-times, 5/2-times, 10/3-times, 5-times, 10-times, 20-times, and 40-times, and 10 concentrations were prepared as amino acids for measurement.

After 75 µL of the internal standard solution of the present invention of Example 2 was added to 75 µL of the external standard solution (plasma balance amino acids mixed standard solution) of Example 1 and mixed well, 150 µL of acetonitrile was added thereto and mixed well. Similarly, after 75 µL of the conventional internal standard solution of Example 2 was added to 75 µL of the external standard solution (plasma balance amino acids mixed standard solution) of Example 1 and mixed well, 150 µL of acetonitrile was added thereto and mixed well.

(2) Precolumn Derivative

With the use of 3-aminopyridyl-N-hydroxysuccinimidyl carbamate reagent, precolumn derivatization was performed. To 185 µL of 200 mM borate buffer solution (pH 8.8), 10 µL of the solution including the internal standard solution of the present invention of the above described (1) was added, and mixed well. Further, 5 µL of 3-aminopyridyl-N-hydroxysuccinimidyl carbamate reagent (the one which was prepared by dissolving 20 mg in 1 mL of acetonitrile) was added and mixed well, then warmed at 60° C. for 5 minutes, and used it as a sample for analysis. Similarly, to 185 µL of 200 mM borate buffer solution (pH 8.8), 10 µL of the solution including the conventional internal standard solution of the above described (1) was added, and mixed well. Further, 5 µL of 3-aminopyridyl-N-hydroxysuccinimidyl carbamate reagent was added and mixed well, then warmed at 60° C. for 5 minutes, and used this as a sample for analysis as comparative example.

(3) Analysis with High Performance Liquid Chromatography-Mass Spectrometry System The above described sample for analysis was analyzed by the following conditions, respectively:

High performance liquid chromatography: 20A series (Shimazu Corporation);

Analytical column: Inertsil ODS-3 (GL Science Inc.);

Prefilter: 0.5 µm disk, for prefilter (Shimazu Corporation);

Mobile phases: Mobile phases A: 25 mM formic acid (pH was adjusted to 6.0 with aqueous ammonia);

Mobile phases B: Acetonitrile;

Column temperature: 40° C.;

Sample injection volume: 5 µL;

Mass spectrometer: LCMS2020 (Shimazu Corporation);

Monitor ion:

$EtONH_2$: 182, Gly: 196, Ala: 210, Sar: 210, GABA: 224, β-AiBA: 224, α-ABA: 224, Ser: 226, Pro: 236, Val: 238, Thr: 240, Tau: 246, HyPro: 252, Ile: 252, Leu: 252, Asn: 253, Asp: 254, Gln: 267, Glu: 268, Met: 270, His: 276, α-AAA: 282, Phe: 286, 1MeHis: 290, 3MeHis: 290, Arg: 295, Cit: 296, Tyr: 302, Trp: 325, Car: 347, Ans: 361, Orn: 373, Lys: 387, δ-HyLys: 403, $Cys_2$: 481.

After the measurement, using the measurement results, normalized response factor was calculated. That is, the response factors were calculated by dividing the peak area ratio by the concentration value, and the response factors were standardized by regarding the response factors of the concentration 8 as 1.0.

The following table 7 shows the response factor obtained from the result used internal standard solution of the present invention, and Table 8 shows the response factor obtained from the result used the conventional internal standard solution. It should be noted that Table 7 and 8 indicate only about amino acids from which internal standard solution differs.

It should be noted that, based on the above described results, the one, in which difference in linearity between Example and Comparative Example was observed, was given gray color in framework in the table (gray: corresponds to the concentration range from the minimum concentration to the maximum concentration of the amino acid in human plasma shown in Table 3), and aside of each abbreviation for amino acid, ⊚: difference between Example and Comparative Example was greater than 0.3 in the gray part, ○: the difference was 0.2 to 0.3, ∆: the difference was 0.1 to 0.2, ▲: the difference was less than 0.1 were added, respectively. In addition, * represents the one from which the labeled element differs among those in which such a difference has been observed, and ** represents the one in which stable isotope of different amino acid is used, among those in which such a difference has been observed.

TABLE 7

Concentration of external standard solution

| Amino Acid | Conc. 1 | Conc. 2 | Conc. 3 | Conc 4 | Conc. 5 | Conc. 6 | Conc. 7 | Conc. 8 | Conc. 9 | Conc. 10 |
|---|---|---|---|---|---|---|---|---|---|---|
| Asp | 0.93 | 0.90 | 0.94 | 0.89 | 0.92 | 0.93 | 0.93 | 1.00 | 1.01 | 1.33 |
| Asn ▲** | 0.99 | 0.99 | 1.00 | 0.99 | 0.97+ | 0.99+ | 0.98+ | 1.00+ | 1.04 | 1.03 |
| Gly Δ* | 0.93 | 0.95 | 0.96+ | 0.96+ | 0.97+ | 0.96+ | 0.98+ | 1.00+ | 0.98 | 1.01 |
| His | 0.96 | 0.97 | 0.95 | 0.96 | 0.96 | 0.97 | 0.97 | 1.00 | 0.98 | 1.00 |
| Cit | 0.91 | 0.94 | 0.98 | 0.94 | 0.96 | 0.93 | 0.98 | 1.00 | 1.01 | 1.02 |
| Tau ☺** | 0.83 | 0.85 | 0.89+ | 0.89+ | 0.91+ | 0.94+ | 0.98+ | 1.00+ | 1.14+ | 1.23 |
| Thr | 0.96 | 0.96 | 0.99 | 0.95 | 0.98 | 0.96 | 0.99 | 1.00 | 1.02 | 1.04 |
| Pro ☺* | 1.01+ | 0.99+ | 0.99+ | 1.01+ | 1.01+ | 0.97+ | 1.00+ | 1.00 | 1.01 | 1.04 |
| Tyr Δ** | 0.98 | 0.99 | 0.99 | 0.99 | 0.98 | 0.99+ | 1.00+ | 1.00+ | 0.99+ | 1.00 |
| Val ○* | 0.98 | 0.97 | 0.97 | 0.97 | 0.96 | 0.97 | 0.99 | 1.00 | 0.99 | 1.01 |
| Met Δ* | 0.97+ | 0.98+ | 0.99+ | 0.99+ | 0.99+ | 0.99+ | 0.98+ | 1.00 | 0.99 | 1.02 |
| Orn | 1.03 | 1.00 | 1.03 | 0.99 | 1.03 | 0.99 | 1.02 | 1.00 | 1.03 | 1.04 |
| Lys | 0.96 | 0.97 | 0.97 | 0.96 | 0.97 | 1.01 | 0.98 | 1.00 | 1.00 | 0.99 |
| Ile ▲** | 0.96 | 0.95 | 0.95 | 0.97 | 0.97 | 0.96+ | 0.98 | 1.00+ | 0.99+ | 0.99 |
| Phe ▲** | 0.96 | 0.97 | 0.98 | 0.97 | 0.97 | 0.97+ | 0.96+ | 1.00+ | 0.98 | 0.98 |
| Trp Δ** | 1.01 | 1.00 | 1.00 | 1.00+ | 1.01+ | 1.00+ | 1.00+ | 1.00+ | 1.03 | 1.02 |

TABLE 8

Concentration of external standard solution

| Amino acid | Conc. 1 | Conc. 2 | Conc. 3 | Conc. 4 | Conc. 5 | Conc. 6 | Conc. 7 | Conc. 8 | Conc. 9 | Conc. 10 |
|---|---|---|---|---|---|---|---|---|---|---|
| Asp | 0.97 | 1.00 | 0.97 | 0.96 | 0.95 | 0.96 | 0.98 | 1.00 | 1.08 | 1.22 |
| Asn ▲** | 0.84 | 0.87 | 0.89 | 0.92 | 0.94+ | 0.98+ | 0.99+ | 1.00+ | 1.02 | 1.03 |
| Gly Δ* | 0.74 | 0.78 | 0.83+ | 0.86+ | 0.88+ | 0.93+ | 0.96+ | 1.00 | 1.01 | 1.05 |
| His | 0.97 | 0.96 | 0.97 | 0.98 | 0.99 | 1.00 | 0.98 | 1.00 | 1.03 | 1.03 |
| Cit | 0.89 | 0.91 | 0.93 | 0.94 | 0.95 | 0.97 | 0.98 | 1.00 | 1.01 | 0.99 |
| Tau ☺** | 1.56 | 1.49 | 1.54+ | 1.26+ | 1.35+ | 1.31+ | 1.14+ | 1.00+ | 0.98+ | 1.01 |
| Thr | 1.04 | 1.05 | 1.05 | 1.01 | 1.04 | 1.05 | 1.02 | 1.00 | 1.00 | 1.00 |
| Pro ☺* | 0.46+ | 0.51+ | 0.57+ | 0.61+ | 0.67+ | 0.74 | 0.83+ | 1.00 | 1.08 | 1.11 |
| Tyr Δ** | 0.62 | 0.67 | 0.74 | 0.75 | 0.80 | 0.86+ | 0.92+ | 1.00+ | 1.03+ | 1.04 |
| Val ○* | 0.66 | 0.69 | 0.72 | 0.73 | 0.75+ | 0.83+ | 0.90+ | 1.00 | 1.17 | 1.24 |
| Met Δ* | 0.82+ | 0.86+ | 0.86+ | 0.89+ | 0.91+ | 0.95+ | .0.96+ | 1.00 | 1.03 | 1.03 |
| Orn | 1.01 | 0.99 | 1.01 | 1.01 | 0.99 | 1.03 | 1.02 | 1.00 | 1.00 | 1.01 |
| Lys | 0.96 | 0.97 | 0.99 | 0.97 | 0.97 | 1.01 | 1.01 | 1.00 | 1.01 | 1.02 |
| Ile ▲** | 0.72 | 0.75 | 0.78 | 0.79 | 0.82 | 0.89+ | 0.93+ | 1.00+ | 1.06+ | 1.11 |
| Phe ▲** | 0.82 | 0.87 | 0.87 | 0.87 | 0.90 | 0.95+ | 0.98+ | 1.00+ | 1.01 | 1.05 |
| Try Δ** | 1.11 | 1.16 | 1.14 | 1.09+ | 1.11+ | 1.13+ | 1.08+ | 1.00+ | 0.95 | 0.94 |

It turned out that when the internal standard solution of the present invention was employed, as compared with the conventional internal standard solution, the linearity of Asn, Gly, Tau, Pro, Tyr, Val, Met, Ile, Phe, and Trp were improved. That is, it was suggested that the internal standard solution of the present invention can give a quantitativity for wide concentration range, and it would be quite useful in determination of amino acids in a biological sample. In addition, it turned out that, in the amino acid concentration range (gray parts in the table) in human plasma, as compared with the conventional internal standard solution, the linearity has been improved particularly in Gly, Tau, Pro, Tyr, Val, Met, and Trp, and among them, the linearity has been improved especially in Tau and Pro.

Other embodiment which may be derived by combining the above described each embodiment, or by adding various changes by the method well known to those skilled in the art is also included in the scope of the present invention.

INDUSTRIAL APPLICABILITY

The present invention, in the quantitative analysis of amino acid in plasma, is intended to provide an external standard solution which is consistent with the existence concentration of amino acid of the object for analysis, and a method for quantitative method of amino acid using said external standard solution. Thereby, the number of calibration points for making up a calibration curve can be reduced, and also the concentration range of the amino acid of the object for analysis can be narrowed down and the quantitative analysis of the amino acid with higher accuracy become possible. Therefore, the present invention provides a significant effect as compared with the conventional technology, and is extremely useful.

REFERENCE SIGNS LIST

In the FIGURE, —□— represents the average concentration of various kinds of amino acid of 6469 specimens measured in Experimental Example 1; —♦— represents the average concentration +2 SD (standard deviation) of various kinds of amino acid measured in Experimental Example 1; —▲— represents the average concentration −2 SD (standard deviation) of various kinds of amino acid measured in Experimental Example 1; —◇— represents the external standard solution (concentration 1) of the present invention prepared in Example 1; —○— represents the external standard solution (concentration 5) of the present invention prepared in Example 1; —*— represents the conventional amino acids mixed standard solution (concentration 1')

prepared in Comparative Example 1; and —○— represents the conventional amino acids mixed standard solution (concentration 5') prepared in Comparative Example 1; respectively. In addition, bars prolonged up and down represent the maximum and the minimum values at the time of measuring the amino acids of 6469 specimens.

What is claimed is:

1. An internal standard solution comprising: proline, glycine, valine, methionine, tryptophan, tyrosine, and taurine, wherein one or more atoms of each amino acid is labeled with a stable isotope, and wherein proline has a lower concentration in the internal standard solution than glycine, valine, methionine, tryptophan, tyrosine, and taurine.

2. The internal standard solution according to claim 1, further comprising isoleucine, phenylalanine, and asparagine, wherein one or more atoms of each amino acid is labeled with a stable isotope, and wherein proline has a lower concentration in the internal standard solution than glycine, valine, methionine, tryptophan, tyrosine, taurine, isoleucine, phenylalanine, and asparagine.

3. The internal standard solution according to claim 2, further comprising ornithine, ethanolamine, glutamic acid, 3-methylhistidine, serine, histidine, and arginine, wherein one or more atoms of each amino acid is labeled with a stable isotope, and wherein proline has a lower concentration in the internal standard solution than glycine, valine, methionine, tryptophan, tyrosine, taurine, isoleucine, phenylalanine, asparagine, ornithine, ethanolamine, glutamic acid, 3-methylhistidine, serine, histidine, and arginine.

4. The internal standard solution according to claim 1, wherein proline has a lower concentration than all other amino acids in the internal standard solution.

5. The internal standard solution according to claim 1, wherein taurine has a higher concentration in the internal standard solution than proline, glycine, valine, methionine, tryptophan, and tyrosine.

6. An internal standard substance, wherein said internal standard substance is obtained by lyophilizing the internal standard solution of claim 1.

7. A method for analyzing amino acids in plasma, the method comprising (i) preparing an internal standard solution according to claim 1; (ii) adding the internal standard to a plasma sample; (iii) analyzing the amino acids and the internal standard in the plasma sample by separation analysis; and (iv) determining a concentration of the amino acids in the plasma sample based on results obtained from the internal standard.

8. The method of claim 7, wherein the separation analysis is conducted by liquid chromatography-mass spectrometry.

9. An internal standard solution comprising: proline, glycine, valine, methionine, tryptophan, tyrosine, and taurine, wherein one or more atoms of each amino acid is labeled with a stable isotope, and wherein taurine has a higher concentration in the internal standard solution than proline, glycine, valine, methionine, tryptophan, and tyrosine.

10. The internal standard solution according to claim 9, further comprising isoleucine, phenylalanine, and asparagine, wherein one or more atoms of each amino acid is labeled with a stable isotope, and wherein taurine has a higher concentration in the internal standard solution than proline, glycine, valine, methionine, tryptophan, tyrosine, isoleucine, phenylalanine, and asparagine.

11. The internal standard solution according to claim 10, further comprising ornithine, ethanolamine, glutamic acid, 3-methylhistidine, serine, histidine, and arginine, wherein one or more atoms of each amino acid is labeled with a stable isotope, and wherein taurine has a higher concentration in the internal standard solution than proline, glycine, valine, methionine, tryptophan, tyrosine, isoleucine, phenylalanine, asparagine, ornithine, ethanolamine, glutamic acid, 3-methylhistidine, serine, histidine, and arginine.

12. The internal standard solution according to claim 9, wherein taurine has a higher concentration than all other amino acids in the internal standard solution.

13. An internal standard substance, wherein said internal standard substance is obtained by lyophilizing the internal standard solution of claim 9.

14. A method for analyzing amino acids in plasma, the method comprising (i) preparing an internal standard solution according to claim 9; (ii) adding the internal standard to a plasma sample; (iii) analyzing the amino acids and the internal standard in the plasma sample by separation analysis; and (iv) determining a concentration of the amino acids in the plasma sample based on results obtained from the internal standard.

15. The method of claim 14, wherein the separation analysis is conducted by liquid chromatography-mass spectrometry.

* * * * *